US005578460A

United States Patent [19]
Ebersole et al.

[11] Patent Number: 5,578,460
[45] Date of Patent: Nov. 26, 1996

[54] ELECTROPHORETIC METHOD FOR THE ISOLATION AND SEPARATION OF MICROORGANISMS AND CELL POPULATIONS

[75] Inventors: Richard C. Ebersole, Wilmington; John G. DeCarolis, Newark, both of Del.; Randy M. McCormick, Santa Clara, Calif.

[73] Assignee: E. I. Du Pont de Nemours and Company, Wilmington, Del.

[21] Appl. No.: 424,753

[22] Filed: Apr. 18, 1995

Related U.S. Application Data

[63] Continuation-in-part of Ser. No. 125,956, Sep. 23, 1993, abandoned.

[51] Int. Cl.$^6$ ............... C12Q 1/02; C12Q 1/24; C12N 13/00
[52] U.S. Cl. ............ 435/29; 435/30; 435/34; 435/173.9; 356/344
[58] Field of Search ............... 435/29, 30, 34, 435/173.9; 204/180.1, 299 R, 300 EC, 153.12; 356/344

[56] References Cited

U.S. PATENT DOCUMENTS 5,324,401  6/1994  Yeung et al. .................. 204/180.1

OTHER PUBLICATIONS

McCormick, R., Capillary Zone Electrophoretic Separation of Peptides and Proteins Using Low pH Buffers in Modified Silica Capillaries, Anal Chem 1988 60, 2322–2328.

*Primary Examiner*—Ralph J. Gitomer

[57] ABSTRACT

The present invention sorts microorganism populations from a mixture which contains more than one microorganism population. Microorganisms of different types vary in size, shape, and surface charge characteristics. These characteristics we believe contribute to the rate of migration for microorganisms under the influence of an electric field. Microorganisms of the same population (genus and species) will migrate similarly. By applying an electric field in a direction opposite the direction of fluid flow, separation is enhanced.

10 Claims, 6 Drawing Sheets

ELECTROPHORETIC METHOD FOR THE ISOLATION AND SEPARATION OF MICROORGANISMS AND CELL POPULATIONS

This is a continuation-in-part of Ser. No. 08/125,956, filed on Sep. 23, 1993 now abandoned.

FIELD OF INVENTION

The invention relates to a method and apparatus for capillary electrophoretic separation and isolation of populations of living cells and subsequent collection of viable cells into discrete fractions for identification or other analysis. More particularly, a mixture of viable biological cells is introduced into a capillary electrophoresis tube. The application of an electric field then causes migration and separation of cells to the end of the capillary tube which is in contact with a collection device. In one embodiment, the collection system allows for the sorting and deposition of cells onto a nutrient gel for growth, thereby producing a "biogram" of the population of cells separated in the capillary. Alternatively, cells can be collected into tubes or collected onto membranes for analysis. The collection system facilitates analysis of the cells being migrated and/or separated.

BACKGROUND OF THE INVENTION

Isolation of microorganisms from mixed microbial populations is fundamental to the practice of bacteriology and microbiology. In the past, isolation has involved two general approaches, single cell and fractionation methods. Techniques such as cell plating, cell sorting (Shapiro, H. M., ASM News, 56, 584, 588, (1990) and Shapiro, J. A. 1991, ASM News, 57, 247, (1991) and micromanipulation, operate at the single cell level. These methods rely on spatially separating the mixed population into individual organisms and subsequently allowing each to grow into individual colonies (Johnstone, H. *Methods of Microbiology*, Vol. 1, Academic Press, Inc., New York 455–471 J. R. Norris and D. W. Ribbons (ed.) (1969)). Single cell techniques are capable of high resolution but tend to select for specific cell types while potentially ignoring a preponderance of other organisms present in the sample. Fractionation techniques, such as selective culture, differential centrifugation, filtration, and adsorption methods operate at the population level. These methods fractionate mixtures into sub-populations based on biological, chemical, or physical differences among the individual groups of organisms (Veldkamp, H., *Methods of Microbiology*, Vol. 3A, p. 305–361 Academic Press, Inc., New York J. R. Norris and D. W. Ribbons (ed) (1970)). Fractionation approaches tend to have limited resolution. Typically, one or more groups of cell types can be selectively recovered from a mixture using fractionation approaches. However, resolving all sub-populations of a mixture into individual pure fractions is difficult to achieve. Furthermore, fractionation methods can distort the relative numbers or types of organisms in the original sample by selecting for or killing off specific sub-populations. Currently, neither single cell nor fractionation methods provide reliable assessment of the quantitative composition of microbial mixtures. Investigating the composition of mixed microbial populations, thus, continues to be a technical challenge (Herbert, R. A., *Methods in Microbiology*, Vol. 22, p. 1–33, Academic Press, Inc., New York, R. Grigorva and J. R. Norris (ed.) (1990)). Technology enabling the quantitative separation and recovery of viable microorganisms from mixed populations is a continuing unmet need.

Electrophoresis is the migration of charged substances in a conductive solution under the influence of an electric field. Separation of substances is achieved according to their net surface charge density. Anticonvective media can be interdisposed in the electrophoretic chamber to effect separations based on sieving and other physical interactions. By this means, differences in molecular size and shape can be detected. Anticonvective materials suitable for electrophoresis may include silica gel, glass wool and asbestos, cellulose fibers, sucrose density gradients, cellulose acetate, as well as gel matrices such as gelatin, agar, starch, polyacrylamide, agarose and mixed polymers (Tietz D., *J. Chromatogr.*, 418, 305, (1987)).

Generally anticonvective materials are too restrictive to permit cell migration through the electrophoretic matrix. Therefore, a variety of non-sieving separation electrophoresis techniques has been developed over the years to effect separation of cells in an electric field. These generally use free flow electrophoretic techniques in which cells are migrated through a homogeneous electrolyte buffer solution. Free flow methods may include static techniques such as microelectrophoresis, density gradient electrophoresis or continuous flow electrophoresis techniques such as Continuous Free Flow Electrophoresis (CFFE) and capillary electrophoresis (CE).

Microelectrophoresis involves the direct microscopic observation of visible particles as they migrate in an electric field. The particles, suspended in buffer, are placed in a transparent rectangular or cylindrical chamber. An electric field is then applied across the chamber. The time required for a particle to cover a given distance is measured in a micrometer eyepiece and noted. The results are expressed as mobility per unit field strength (electrophoretic mobility).

Various attempts to characterize electrophoretic mobility of biological cells and viruses using microelectrophoresis methods have been recited in the art. Richmond, D. V., et al., (*Advances in Microbial Physiology*, 9,1, Ed., A. H. Rose and D. W. Tempest Academic Press, London (1973)) reviewed work regarding electrophoretic mobilities of various classes of viruses, bacteria, trypanosomes, fungi and algae using microelectrophoresis techniques. Work by Bayer, M. E. et al., (*J. General Microbiology* 136, 867, (1990)), using a Penkem S3000 electrokinetic analyzer, describes the electrokinetic characterization of the charge on Gram-positive and Gram-negative bacteria. Additionally Grotenhuis, J. T. C., et al., (*Appl. Environ. Microbiol.*, 58, 1054, (1992)) teach that seven species of methanogenic bacteria demonstrate significant differences in electrophoretic mobility.

Microelectrophoresis techniques are useful in quantitative measurement of surface charge on individual cells. These studies clearly substantiate differences in surface charge and electrophoretic differences between many microorganisms and different animal cell types. These differences potentially could be useful in separation and recovery of cell populations. However, microelectrophoresis methods do not provide means of quantitative characterization, separation, and recovery of cell populations. Microelectrophoretic measurements require tracking and measuring the rate of migration of individual cells, making the method cumbersome and time consuming. Thus only a small proportion of the total numbers of cells can be characterized. Most importantly, the potential for cell separation is diminished since resolution between cells depends only on differences in one vector force e.g., electrophoretic mobility, and short electrophoresis times.

Other electrophoretic techniques have, however, been used to characterize microorganism populations and explore their separation. Generally these involve a variation of "Continuous Free-Flow Electrophoresis" (CFFE) in which migration is carried out without convective stabilization materials. Separation is achieved in thin films of fluid flowing between two parallel plates. An electric field is applied perpendicular to the direction of electrolyte flow. The electrolytes and sample are pumped through the separation chamber and are collected in an array of collection ports at the opposite end of the separation chamber.

A typical CFFE apparatus comprises a linear separation chamber filled with a separation buffer and bounded on each side by electrodes, across which an electrical potential is maintained perpendicular to the fluid flow. Separation buffer is pumped at a constant flow rate through the chamber from an inlet port to the fraction collecting outlet ports. A mixture of cells is injected at the inlet port of the separation chamber along the edge of the cathode electrode and electrophoretic migration occurs laterally across the width of the separation chamber. The continuous flow of the separation buffer carries the migrated cells to the outlet end of the chamber where they exit into an array of collection ports for analysis (Todd, P., In *Cell Separation Science and Technology*, 216, A.C.S., Washington, D.C. (1991)).

Continuous Free Flow Electrophoresis (CFFE) has been popular in hematology for the separation of various blood cells and blood components. For example Crawford, N., et al., (In *Cell Separation Science and Technology*, 190, A.C.S., Washington, D.C. (1991)) disclose the separation of neutrophils from human whole blood using CFFE, whereas Hanse, E., et al., (*Electrophoresis*, 10, 645, (1989)) discuss the separation of antigen positive and antigen negative human blood lymphocytes and Hannig, K., et al., (*Electrophoresis*, 11, 600, (1990) demonstrate the use of CFFE for the separation of rabbit, guinea pig and rat erythrocytes.

CFFE methods has also been applied to separation of microorganisms. Fedorikina, O. A., et al., (*Mikrobiol. Zh.*, 48, 83, (1986)) compare the use of three electrophoretic methods in the separation of a mixed population of bacterial cells. The three methods encompassed sucrose density gradient, isotachophoresis and pH gradient electrophoresis. pH gradient electrophoresis effectively separated a mixed population of *E. coli* and *S. aureus* into pure populations. Greater specificity has been demonstrated by Hansen-Hagge, T., et al., (Eur. J. Biochem.,148, 24, (1985)) where free flow electrophoresis was demonstrated to be effective in the separation of *S. typhimurium* lipid A defective mutants from wild type cells. Cells were applied directly to the chamber buffer and fractions were collected over time. This method separated cells deficient in the production of lipid A from the wild type population. Uhlenbruck, G. A., et al., (*Zbl. Bakt. Hyg.*, A 270, 28, (1988)) using a similar "carrier free averting electrophoresis" device for the separation of Group B streptococcus types.

As noted above, CFFE approaches have shown promise for separation and recovery of biological cells. However, CFFE resolution is inherently limited and of marginal. Cell resolution of CFFE relies both on differences in electrophoretic mobility due to differences in surface charge as well as on differences in cell/fluid interactions created when cells interact with the flow of electrolyte fluid. Electrolyte flow in CFFE is laminar and consequently nonuniform across the electrophoretic chamber. At the boundary surfaces of the chamber, electroosmotic flow can further distort the uniformity of electrolyte flow. Furthermore convection currents within the chamber due to Joule heating, vibration and gravitational effects can further distort the uniformity of electrolyte flow with in the separation chamber. As a consequence, cell/fluid interactions are inherently non-uniform, making electrophoretic migration variable and consequently reducing the inherent electrophoretic resolution. Positioning of fraction collecting ports is thus difficult to predict. Attempts to offset these distortions by performing CFFE separations in space (zero gravity) have proved only marginally effective (Todd, P., In *Cell Separation Science and Technology*, 216, A.C.S., Washington, D.C. (1991)). Potential resolution between cell populations is further restricted by the limited number of fraction collection ports. Limitations on the number of ports that can be designed and mechanically built into the system restricts the number of fractions into which cell populations can be subdivided and limits the ability to discriminate between closely related populations.

Another free flow electrophoretic method is capillary electrophoresis (CE). CE has developed into a powerful analytical separation technique and is particularly useful when sample size is limited since very small sample volumes can be introduced into narrow bore capillary tubes (0.01 to 0.10 mm) for separation. In free solution capillary electrophoresis, the capillary tube is filled with an electrolyte solution, and when an electric field is applied across the capillary, solutes migrate from one electrode toward the other electrode based on the sum of the electrophoretic mobility of the solute and the electroosmotic mobility of the bulk flow of the electrolyte. Because of the small diameter of the capillary, heat is dissipated efficiently, allowing separations to be accomplished at high voltages without distortion from Joule heating. This results in very fast separations without significant loss of resolution. (Jones, H. K., et al., Anal. Chem., 62,2484, (1990); McCormick, R. M., J. Liq. Chromatography, 14, 939, (1991)). However, the high ratio of surface area to electrolyte volume in a capillary can promote both adsorption of solutes onto the capillary walls and distortion of electrophoretic mobility due to electroomotic flow. Both factors can diminish analytical resolution. Typically, these are overcome by chemically passivating the wall of the capillary to diminish electroosmotic flow and reduce adsorption.

Using this technique, Hjérten et al. (*J. Chromatogr.*, 403, 47, (1987)) have shown that movement of the bacterium *Lactobacillus casei* can be accomplished through a fused-silica tube. The bacteria was sucked into a 115 μm fused silica tube, a voltage applied, and migration occurred toward the anode. The fused-silica tube had been coated with a polymer to suppress electroosmosis and adsorption; as a consequence, movement of the bacteria occurred from the cathode to the anode, based on its negative charge. However, no separation or resolution of bacteria was achieved or disclosed and movement of the bacteria was strictly on the basis of its surface charge. Furthermore, a mechanism for separation and recovery of the isolated bacteria was not disclosed.

Several methods of collecting eluted solutes from CE systems have been reported in the art. For example, Huang et al., (*J. Chromatogr.* 516, 185, (1990)) have devised a method of fraction collection for capillary electrophoresis which allows continuous contact of the capillary with electrolyte buffer while the analyte is eluting onto a roller covered with filter paper. For collection of materials, this system employs an on-column frit structure to maintain electric continuity between the electrode, cathode buffer reservoir and column buffer. The porous frit structure is constructed about 1–2 cm from the exit end of the capillary tube. This frit allows electrical connections to be made to the capillary, as it is submerged into a buffer reservoir. Two significant drawbacks to the method of Huang are, first, that the porous frit is difficult to construct, and second, sample leaking out of the frit into the buffer reservoir can occur. A further disadvantage of this method is that the system relies on continuous streaking of the sample materials, and does not provide a means of discontinuous programmed deposition of sample fractions in discrete wells or tubes.

In U.S. Pat. Nos. 4,631,120 and 4,631,122, Pohl discloses an apparatus and method for collection of "elemental particles" onto a moving "collecting tape" that are eluted from a porous paper matrix or gel after electrophoretic separation. The system does not provide a means of separation and collection of cells since cell migration is obstructed by molecular sieving effects of the gel and paper separation matrices. Furthermore, the collection tape only moves in one direction and provision is made for X, Y, Z motion of the electrophoretic chamber. Thus the system does not provide for discontinuous sorting and deposition of sample fractions.

U.S. Pat. No. 5,126,025 describes a method and apparatus for collecting CE fractions separated onto a porous layer that retains the solute. A sandwich type collection assembly comprised of three layers is described. The top layer is the porous layer where the sample is deposited. The middle layer is the wetted absorbent layer which maintains electrical continuity. The bottom layer is an electrically conductive plate, attached to the cathode electrode. The exit end of the capillary is in contact with the porous layer, thereby depositing the solute onto the porous layer as the solute is eluted from the capillary end. Collection and deposition of the fractions are accomplished by moving the entire sandwich collection assembly in a circular motion during deposition of the sample. In another mode, the sample can be deposited onto a rotating cylinder. A disadvantage of this apparatus is that the capillary remains in a fixed position. Contact of the capillary and porous layer must be continuous, prohibiting different modes of collection, such as deposition of the solute into tubes or multiwell plates. Thus, the system does not provide for discontinuous sorting or deposition of sample fractions in tubes, microwells or onto solid supports.

There exists a need, therefore, for a method to separate bacterial and other biological cell mixtures into discrete fractions without upsetting the relative distribution of the cells in the original sample, while maintaining the viability of the cells. Furthermore, there is a need to provide a cell collection system enabling individual cells and cell fractions to be sorted and collected in microwell receptacles, tubes, and onto planar supports.

The instant method seeks to meet these needs by providing a novel cell separation method and apparatus for cell collection. Typically, capillary electrophoresis is subject to the complicating forces of high temperature and electroosmotic flow which would be expected to limit viability of the cells and interfere with bacterial and other particle separations (Jones, H. K., et al., *Anal. Chem.*, 62, 2484, (1990); McCormick, R. M., *J. Liq. Chromatography.*, 14, 939, (1991)). The instant method has overcome these problems by utilizing the highly unexpected finding that cells can be separated within a small bore capillary tube by exploiting the resultant effects of two opposing vector forces, electroosmotic flow and electrophoretic mobility. Using this approach, clear separation of cell populations can be achieved.

SUMMARY OF THE INVENTION

It is an object of the invention to provide a novel electrophoretic method for the separation of viable mixtures of viable bacteria for analysis of microbial communities. The instant method utilizes a small bore capillary tube filled with a suitable electrolyte and the counteracting forces of both an electrophoretic field and an electroosmotic flow to effect a highly specific separation of bacterial and other biological cells.

Furthermore, it is also an objective to provide a method to isolate and collect the separated bacterial fractions, using a computerized automated robotics collection device. The invention further provides an apparatus and a means to dispense the separated bacterial fractions by streaking them onto the surface of a nutrient agar gel plate, in this way providing a biogram of cell composition and cell numbers.

The invention also provides means of collection in which the bacterial fractions can be dispensed into tubes, multiwell devices or deposited onto planar supports and membranes, which would allow further biochemical analysis, such as identification, microscopy, immunoassays, DNA assays, etc. Sorting of the fractions can also be accomplished by using multiple detectors, which can discriminate a particular cell type having a specific detector or electrophoretic response, then transported automatically to a specified location or collection vessel.

A sample of a bacterial mixture is introduced into the anodic end of the capillary tube, either by siphoning or electrokinetic injection, that has been filled with an electrically conductive solution. As an electric field is applied to the capillary, both electroosmotic and electrophoretic movements are created, resulting in the separation of the viable bacteria based on differences in their charge and mass. Unexpectedly and as a result of the preponderance of the electroosmotic field, the bacteria migrate backward toward the anode while the bulk electrolyte flow is toward the cathode, and the net movement of buffer and separated bacteria is toward the cathode. As the separated bacteria pass the detector, the computer senses the detector output and determines the elution time for that particular fraction. As the fraction exits the cathode end of the capillary, the dispensing tip is activated automatically, and the material is either deposited onto a nutrient agar gel plate or transferred to some other collection device. If deposited onto an nutrient agar gel plate, the viable bacteria are streaked onto the surface in some predetermined streaking profile, e.g., length of streak line, distance between each line, speed of dispensing tip, etc. Once deposited, the nutrient agar gel is incubated at the proper temperature for growth, and a "biogram" of the original population of bacteria is produced.

Hence it is within the scope of the present invention to provide a method for the separation of viable microorganisms in a device comprised of providing a viable cell separation (a) a small diameter capillary separation tube having a layer of chargeable material distributed along the inner surface of the tube. The chargeable material is capable of maintaining an electrical charge; (b) an anodic electrode positioned at a first end of the tube; (c) a cathodic electrode positioned at a second end of the tube; and (d) an electrolyte solution filling the tube and contacting both the anodic and cathodic electrodes wherein the electrodes are maintained in electrical communication with each other and the tube. A mixture of microorganisms is injected into the first end of the tube. An electrical potential of between about 1 Kv and 40 Kv is applied across the electrodes whereby both an electrophoretic and an electroosmotic force are produced within the electrolyte solution effecting the migration and separation of the viable microorganisms.

It is further within the scope of the invention to provide a method of collecting and identifying microorganisms separated by an electrophoretic process comprising the steps of providing a cell collecting system further comprising: (a) a movable fraction dispensing device capable of dispensing small volume fractions; (b) a solid growth medium capable of supporting the growth of microorganism; (c) a detector means operably connected to the dispensing device and capable of detecting the presence of microorganism in the dispensing device; and (d) a computer for the coordination of the detector and the dispensing device; moving the dispensing device in a specific pattern above the growth medium in response to the detection of microorganisms in the device; collecting the fractions containing the microorganisms on the solid growth medium; incubating the growth medium for a time sufficient to produce individual colonies of microorganism; analyzing the colonies for the presence of specific microorganisms.

The instant method overcomes several of the disadvantages of capillary electrophoresis sample collection system. The instant method provides a programmable sample dispensing mechanism capable of X-Y-Z motion of the capillary allowing for a controlled discontinuous sorting and dispensing capability.

As will be realized by one of skill in the art, the instant method and apparatus have utility for the separation and characterization of microorganisms in samples originating from the areas of clinical diagnostics, food bacterial detection, and environmental remediation efforts. It is contemplated that the present invention may be particularly useful in the tracking of recombinant or adapted organisms in bioremediation and bioreactor processes.

DETAILED DESCRIPTION

Figure 1:
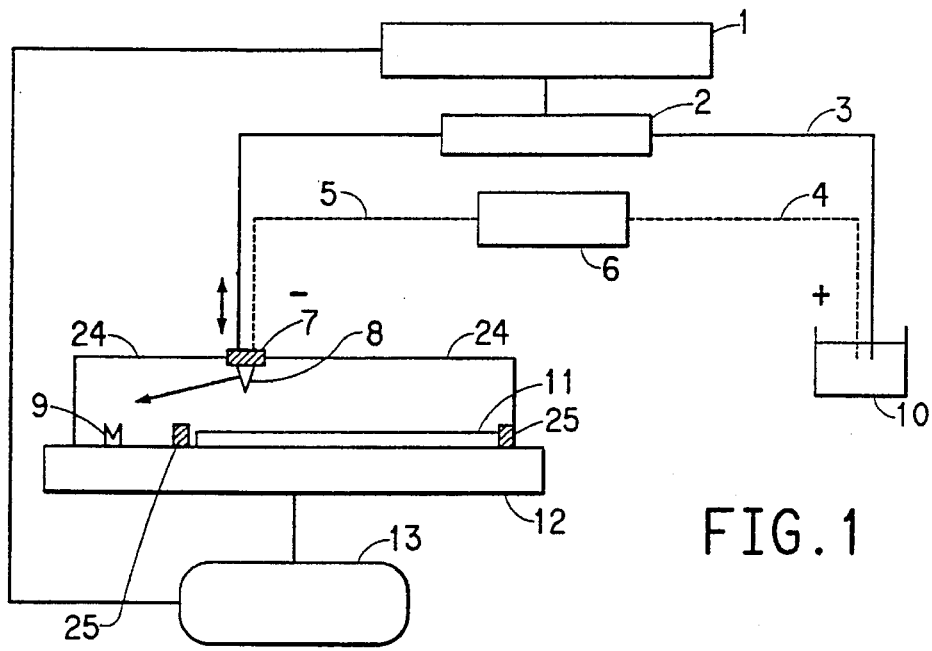
FIG. 1 schematically illustrates components of an electrophoretic sorting and collection system, in which electrophoretic separation, detection and sample collection occurs.

As used herein the following terms may be used for interpretation of the claims and specification.

The term "electrophoretic mobility" refers to the relative mobility of particles when subjected to an electric field.

The term "electrophoretic force" will refer to the that force responsible for production of electrophoretic mobility.

The term "electroosmotic flow" refers to the general flow of electrolyte in a capillary when subject to an electric field, where the net flow of ions in the capillary is toward the electrode of opposite charge to that of the counterion layer. The magnitude of this electroosmotic flow is given by the following equation $$\mu_{eo} = \frac{\epsilon E \zeta}{4\pi\eta}$$

where $\mu_{eo}$ is the linear velocity of transport of the liquid through the capillary tube, $\epsilon$ and $\eta$ are the dielectric constant and viscosity of the liquid media in the capillary, E is the electric field strength, and $\zeta$ is the zeta potential arising from the presence of the accumulated counterions in the double-layer at the wall of the capillary.

The term "electroosmotic force" refers to the force responsible for production of electroosmotic flow.

The terms "counterion layer" or "counterions" refer to the layer of ions within an electrolyte solution which accumulate along the wall of the capillary and carry a charge opposite to the net charge of the wall of the capillary.

The term "electrophoresis" refers to the migration of charged particles in a conductive solution under the influence of an electric field where separation of substances is achieved according to differences in net surface charge density.

The terms "capillary electrophoresis" or "capillary zone electrophoresis" refer to the separation of particles in a system comprising a capillary tube filled with an electrolyte solution, whereby, when an electric field is applied across the capillary, solutes migrate from one electrode toward the other electrode based on the sum of the electrophoretic mobility of the solute and the electroosmotic mobility of the bulk flow of the electrolyte.

The terms "biogram" or "electrophoretic biogram" refer to a separation profile produced by the deposition of eluted cell fractions onto growth media or some solid surface. The profile is formed by the coordination of a cell deposition device with the identification of cell-containing fractions by a detector.

"Biological cell population" refers to a group of cells which possess the same electrophoretic properties.

"Chargeable material" refers to a material which will develop and hold a net negative or positive charge under the influence of an electric field.

The present invention relates to an electrophoretic method and apparatus which achieves separation of microorganisms in a manner which does not alter the relative microbial representation within a given population of cells and individual cells are not disrupted, so that the cells can be recovered in viable form.

The apparatus of the present invention comprises three modules; an electrophoretic separation module comprising a capillary containing an electrolytic buffer and an anodic and cathodic electrode, a sample collection module and a data collection module comprising a detector and a computer.

In one embodiment of the invention, a sample of a mixture of bacterial cells is introduced into the anodic end of the capillary tube that has been filled with an electrically conductive solution. An electric field is applied to the capillary and the bacteria are electrophoretically separated based on differences in their charge, size and mass. The bacteria migrate toward the anode while the bulk electrolyte flow is toward the cathode, and the net movement of buffer and separated bacteria is toward the cathode. As the separated bacteria pass the detector, the computer senses the detector output and determines the elution time for that particular fraction. As the fraction exits the cathode end of the capillary, the material is either deposited onto an nutrient agar gel plate or transferred to some other collection device. If deposited onto an nutrient agar gel plate, the bacteria are streaked onto the surface in a manner determined by some predetermined streaking parameters. Once deposited, the nutrient agar gel is incubated at the proper temperature for biological growth, and a "biogram" of the original population of bacteria is produced.

Electrophoretic Separation—Theory:

Electrophoresis is a separation technique which resolves chemically and/or physically different species into discrete bands based upon differential response to an electric field. A charged particle (of charge q) when subjected to an electric field of strength E will accelerate to a terminal velocity v which is controlled by frictional resistance forces f as described by equation 1:

$$qE = fv \tag{1}$$

which applies when the acceleration due to the electrical field is counterbalanced by viscous drag experienced by the charged particle as it moves through the surrounding medium. The viscous drag resistance is described by Stoke's law as:

$$f = 6\pi\eta r \tag{2}$$

where $\eta$ is the viscosity of the medium through which the charged particle is moving and r is the geometric radius of the charged particle. Combining equations (1) and (2) yields a concise description of the particle's motion through the medium as $$qE = 6\pi\eta v \tag{3}$$

which can be rearranged to give the mobility ($\mu$) of the charged species, $$\mu_{el} = v/E = q/6\pi\eta r \tag{4}$$

where mobility describes the velocity per volt/cm of applied electrical field. Mobility is a convenient term for expressing the relative velocities of various charged species through a medium during electrophoresis as it normalizes for differences in electrical field strengths. Equation (4) reveals mobility of a charged species is a direct function of the magnitude of the electrical charge on the particle, with mobility increasing in a linear relationship with increasing charge q. Equation (4) also shows mobility is inversely related to the size of the charged particle (r), with larger particles having lower mobilities than smaller particles of equal charge. In addition, Equation (4) also shows mobility will vary inversely with the viscosity of the medium through which the particle is moving under the influence of the applied electrical field.

Equation (4) is applicable only to cases where the size of the charged particle is small and consequently the presence of the particle does not distort the applied electrical field and when the ions are at infinite dilution and thus not subject to electrostatic interactions with adjacent charged particles or ions in solution. For the case where the particles are large and thus their presence does alter the electric field and where charged particles exist in a solution of finite ion concentration, a modified form of Equation (4), which applies only to spherical particles, was developed by Henry, D.C., (Proc. R. Soc. A 133 106 (1931)) and is given in Equation (5):

$$\mu_{el} = \frac{q}{6\pi\eta r} \frac{\theta(\kappa r)}{1 + (\kappa r)} \tag{5}$$

where q(Kr) is a function which depends on the effective radius of the particle. The term K is the well-known Debye-Hückel parameter and is given by:

$$\kappa = sqrt \frac{(4\pi Ne^2)}{(1000\epsilon kT)} \; sqrt \, (CZ^2) \tag{6}$$

where N is Avogadro's number, e is the electronic charge, $\epsilon$ is the dielectric constant of the medium through which the particle is moving, k is the Boltzmann constant, T is absolute temperature (Kelvin), C is ionic concentration (moles/liter) and Z is the ion valence.

This equation takes into account that the charged particle will be surrounded by a more or less loosely bound cloud of counterions (ions of charge opposite to the charge on the particle) and this cloud of counter-ions (known as the double layer) will travel with the charged particle, thus increasing its apparent radius to a value greater than the simple geometric radius of the particle and subjecting the particle to greater viscous drag forces than if the counterion layer was absent. Thus, Equation (6) adds another dimension into the determination of the particle's mobility, namely the Debye-Hückel double layer thickness, which is a function of the pH, the chemical composition, and the ionic strength of the solution through which the particle is moving.

In spite of the complexity of the preceding equations, one can readily make conclusions with some degree of accuracy regarding the behavior of charged particles of various sizes if they are placed in a solution in a long cylindrical container and subjected to an electrical field, such as illustrated in FIG. 5. It should be emphasized here, however, that such conclusions are only valid if and when the particles being separated are solid and spherical, having a uniform density and shape.

Figure 5A:
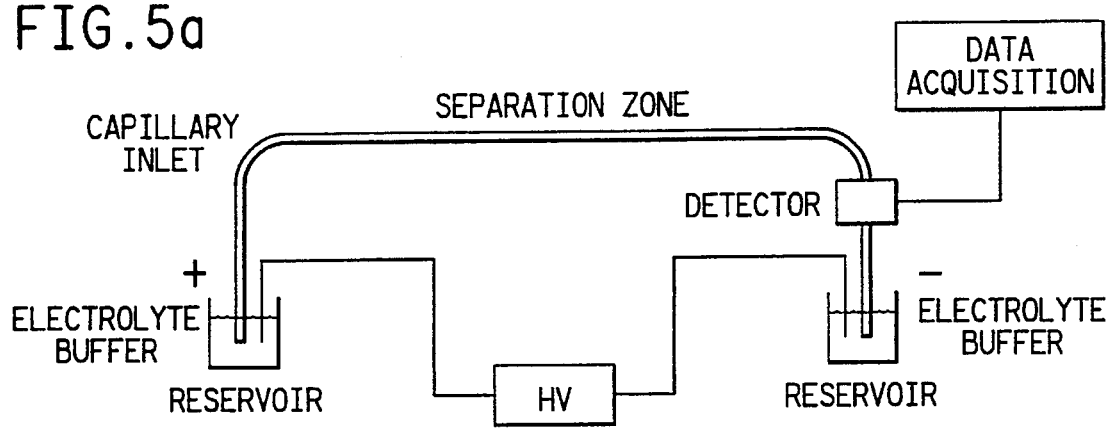
FIG. 5a is a diagram of a capillary electrophoretic separation apparatus. PRIOR ART
Figure 5B:
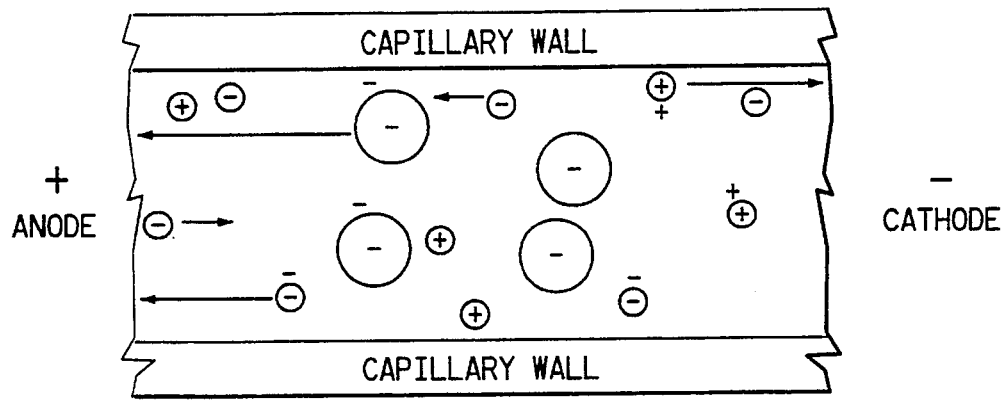
FIG. 5b is a diagram of a typical capillary electrophoretic separation of solid spherical particles of varying sizes and charges. PRIOR ART

FIG. 5b illustrates a typical capillary electrophoretic separation where a small plug of a mixture of small and large spherical particles with one or two negative charges per particle is introduced into a spherical tube and subjected to an electrical field. The negatively charged particles respond to the electrical field by migrating in the direction of charge opposite to the charge on the particles; in this case, the negatively charged particles migrate to the positive electrode. The large, singly charged particles migrate slowest of the three species in the mixture, as they have lower charge and larger mass, thus experiencing greater resistive drag forces as they migrate through the medium in the tube. The small, singly charged particles migrate at a faster rate than the large, singly charged particles and thus travel further towards the positive electrode than the small, singly charged species. Finally, in this example, the large doubly charged particles have greater charge than the other species in this mixture and migrate furthest towards the anode in this experiment. Because of the differences in mobilities of these species when subjected to an electrical field, which arise from differences in particle size and particle charge, it is conceivable to separate a mixture of species of different sizes and charges into discrete bands that contain only species of a single size and charge.

Figure 5C:
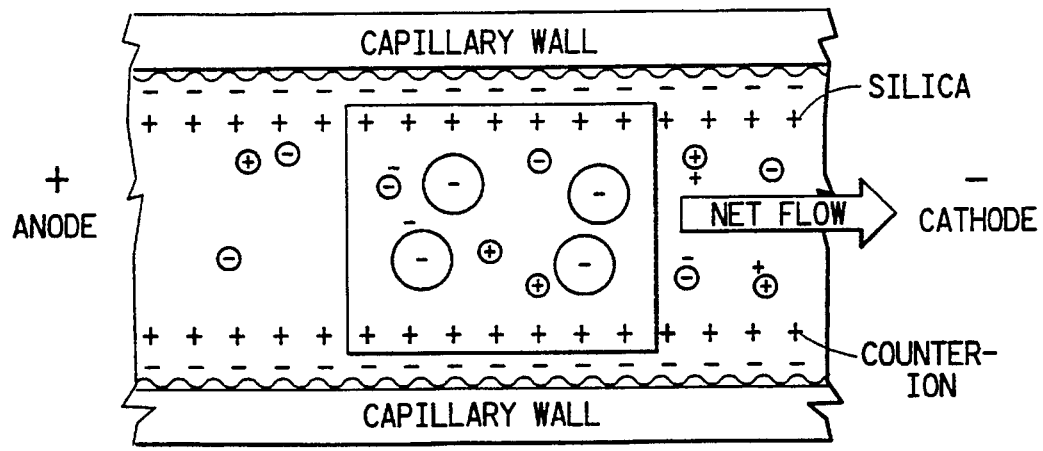
FIG. 5c is a diagram of capillary electrophoretic separation of solid spherical particles of varying sizes and charges when subject to electroosmotic flow as a result of a charged silica coating on the wall of the capillary. PRIOR ART

To effect high resolution separation, one must take precautions that remixing of the separating bands of various particles does not occur during the separation process, which would disrupt or destroy the ongoing separation. One method of guarding against this is to use a small diameter cylindrical capillary tube in which capillary forces between the liquid media in which the separation is occurring and the capillary wall are sufficiently strong as to overcome any mixing forces such as convectional mixing which would diminish or disrupt the quality of the separation. Many types of capillary tubes may be used, where a fused silica capillary is preferred. Fused silica is particularly useful since the charged nature of the wall of the silica capillary, which arises from dissociation of silanol groups on the surface of the silica, gives a negatively charged silica capillary wall with a loosely-attached layer of counterions. On the other hand the presence of this layer of counterions at the silica wall presents an additional complication, since the loose counterion layer will also move under the influence of the applied electrical field. As FIG. 5c illustrates, when these counterions move, they transport along with them the bulk of the water in solution in the capillary, thus establishing what is known as electroosmotic or electroendoosmotic flow. This flow causes the entire contents of the capillary to move (in this case, because the silica wall is negatively charged and the counter-ions are thus positively charged and would move towards the cathode or negative electrode), transporting the ongoing separation towards the cathode or negative electrode. The magnitude of this electroosmotic flow is given by the following equation:

$$\mu_{eo} = \frac{\epsilon E \zeta}{4\pi\eta} \qquad (7)$$

where $\mu_{eo}$ is the linear velocity of transport of the liquid throughout the capillary tube, $\epsilon$ and $\eta$ are the dielectric constant and viscosity of the liquid media in the capillary, E is the electric field strength, and $\zeta$ is the zeta potential arising from the presence of the accumulated counterions present in the double-layer at the wall of the capillary ($\zeta$ is proportional to 1/K, the Debye-Hückel parameter described previously, which relates the influence of the counter-ions on the mobility of charged particles).

The presence of electroosmotic flow has the potential of complicating the separation and protocols are often modified to reduce its effects. With both electroosmotic flow and electrophoresis occurring simultaneously on the separation of the charged particles, transport of the entire contents of the capillary tube towards the cathode occurs while the negatively charged particles migrate against this bulk transport as they try to reach the anode. Consequently, if the magnitude of the electroosmotic mobility is greater than the electrophoretic mobilities of the charged particles, the net result is that transport of the charged particles to the cathode will occur.

In contrast to the art which teaches electroosmotic flow as something to be avoided during particle separation methods, the present invention has produced the unexpected result of being able to utilize the phenomenon of electroosmotic flow to effect the clear and distinct separation of bacterial species and strains. A discussion of this process follows.

Cell Separation:

The preceding theory of electrophoretic capillary separation applies strictly to rigid spherical particles. When the particles to be separated are non-spherical, dynamic entities such as bacterial cells, only the general concepts of the electrophoretic theory may be relied upon. Bacteria are known to have substantial concentrations of negative charges on the outer surface which arise from dissociation of various chemical functionalities such a sialic acid, free carboxylate groups, phosphate groups, etc. These cell surface charge concentrations may be utilized to effect electrophoretic separations. However, bacterial cells are subject to a variety of complicating factors that are not found in particles of fixed form. For example, shape distortion and cell motility as well as the relative distribution of bacteria across the diameter of the capillary due to differences in density of bacteria and the surrounding liquid media will complicate the movement and width of the bands of the bacteria through the capillary as they migrate during separation. Additionally, if one applies the above formulae, it will be seen that all the bacterial cells will be subject to the above identified complicating factor of electroosmotic flow. Hence, the net mobility of the bacteria $\mu_{net}$ through the capillary will be the sum of their electrophoretic and electroosmotic mobilities, e.g., $$\mu_{net} = \mu_e + \mu_{e1} \qquad (8)$$

where $\mu_{eo}$ and $\mu_{e1}$ are defined to be positive in sign for silica capillaries for movement towards to the cathode. Since $\mu_{e1}$ is towards the anode for normally negatively charged bacteria, $\mu_{net}$ will be lower in magnitude than the intrinsic electroosmotic flow in silica capillaries. As long as $\mu_{eo}$ is larger in magnitude than $\mu_{e1}$, however, all of the bacterial species will be carried down the capillary by the prevailing electroosmotic flow.

In spite of these significant complicating factors we have discovered a method of utilizing the effects of electroosmotic flow along with various modifications to cell surface charge and mobilities to achieve distinct separation of bacterial species. For example, the magnitude of the charge on the bacteria can be altered by changing the pH of the separation solution, with substantial changes occurring at solution pH equal to the pK values of the various charged functionalities on the outer surface of the bacterial cell wall (Lemp, J. F., et al., *Biotech. Bioeng.* 13, 17, (1971) and Richmond, D. V., et al., in *Advances in Microbial Physiology*, Ed. A. H. Rose and D. W. Tempest Academic Press, London, Volume 9, pp 1, (1973)).

Treatment of the cells with neuraminidase to remove sialic acid functionalities will also dramatically alter the mobility of the bacteria (G. Uhlenbruck, et al., Zb. Bakt Hyg. A 270, 28, (1988)). Treatment with numerous other specific chemical reagents to convert specific chemical moieties on the surface of the bacterial cell walls have also been suggested. (Richmond, D. V., et al., in *Advances in Microbial Physiology*, Ed., A. H. Rose and D. W. Tempest Academic Press, London, Volume 9, pp 1, (1973)).

The size of the bacteria can also be changed to some degree by osmotically swelling or shrinking the bacteria in solutions of various chemical agents.

Additionally solution viscosity has the potential to affect the mobility and electroosmotic velocity of different bacteria, either accelerating or slowing the speed of the separations. However, one would expect that variations in viscosity would have little effect on the magnitude of the separation of the various species in a mixture. The counterion layer on the silica capillary, which provides a double layer thickness around the charged bacterial species, is responsible for the complexity in determining bacterial electrophoretic mobility. Thus, changes in buffer solution pH or ionic strength or chemical composition will be expected to alter the separation, particularly if different species of bacteria respond to these changes to different degrees. The extent to which the aforementioned variables will affect bacterial cell electrophoretic mobility is difficult to predict a priori without extensive knowledge of the chemical composition of the bacterial cell wall of each species being separated.

It might be expected that changes in the electroosmotic flow (Equation (7)), which transports the separating bacteria through the capillary, could be manipulated by changing the solution pH and/or the ionic strength of the separation buffer to alter bacterial separation patterns. It is known that both the pH (K. D. Lukacs et al., *J. High Res. Chromatogr. Commun.* 8, 407, (1985)) and the ionic strength (D. Altria et al., Anal. Proc. 23, 453, (1986)) affect the double layer thickness of the counterion layer on the silica and can dramatically alter the electroosmotic flow.

All of these factors taken together have the potential to yield a diverse and powerful technique for separating a complex mixture of bacteria of different species into discrete, well-resolved bands.

Apparatus for cell separation and analysis:

In accordance with the applicant's invention, a cell separation and collection apparatus is provided as illustrated in FIG. 1 which comprises a data collection means (1) operably connected to a computer (13) and a detector (2) through which a capillary (3) is positioned. The capillary (3) has a first end submerged in a separation buffer (31) which is in turn contained in a buffer reservoir (10). A second end of the capillary (3) is received by a dispensing tip (8) which is firmly affixed to the capillary (3) and the robotic transport mechanism (24) by a tip clasp (7). A high voltage power supply (6) is electrically connected to an anodic electrode (4) and a cathodic electrode (5). The anodic electrode (4) is submerged in the separation buffer (31) at the first end of the capillary (3) and the cathodic electrode (5) communicates with the second end of the capillary (3) at the point of the dispensing tip (8). The computer (13) is operably connected to the robotic device (12) which comprises a sample collecting receptacle (11) operably connected to a receptacle transport mechanism (25). A dispensing tip reservoir (9) is located to one side of the sample collecting receptacle (11) to receive the dispensing tip (8).

In one embodiment of the invention, a sample of a mixture of viable bacterial cells is introduced into the anode end of capillary (3), which is filled with an electrolyte separation buffer. The electrode buffer may be of the same or different composition as that contained in the sample, and it may contain agents to modulate the electroosmotic flow velocity, or to improve the resolution of the bacterial separation. Generally, electrophoretic buffer must be electrically conductive, facilitate electroosmosis flow and preserve the physiological integrity of the cells. Buffer concentrations can range from 10 μm to 250 mM, more preferably 5 to 150 mM. High buffer molarity can result in high currents that can create excessive Joule heat which can disrupt the separation. Buffer pH is typically between 4 and 9.5, most preferable from pH 7 to 9.0. A preferred separation buffer will consist of 0.05× buffer (TBE) containing 4.45 mM Tris, 4.45 mM boric acid, ph 0.10 mM EDTA and adjusted to pH 9.5 with 10M KOH. Buffers can comprise aqueous solutions of phosphate, borate, tris(hydroxymethyl)aminomethane, "Good" buffer materials (N. E. Good et al., Methods Enzymology, Part B, 24, 532 (1968) and W. J. Ferguson et al., Anal. Biochem.,104, 300 (1980)), aminoethane-sulfonates, and aminopropanesulfonates. The buffer should contain sufficient electrolyte to produce a conductive path within the capillaries in which the separation is to occur. In addition, the buffer should possess sufficient buffering capacity to maintain the pH of the solution within the capillary and in the anode and cathode reservoirs at a constant value during the course of the separation. Typically, the electrolyte is present in the buffer in concentrations of at least 10 μM.

The capillary tube (3), which is typically composed of fused-silica, can be externally coated with a protective polymer. To facilitate transmission or collection of light by a detector, a portion of the outer polymer coating can be removed to create a detection zone or window (flow cell), through which analytes can be detected. Removal of the polymer coating may or may not be required, depending on whether the coating obstructs detection.

In general, capillaries useful in the instant invention have an internal diameter of 5–200 microns. More preferably, the internal diameter ranges from 20 to 100 microns. The external diameter ranges typically from 100 to 500 microns. The length of the capillary will vary with the specific application and electrophoretic conditions. Generally, however, without intending to be limiting, lengths from about 0.1–5 meters can be used, with detection usually occurring toward the terminating end of the capillary. Capillaries suitable for use in the present invention may be purchased from Polymicro Technologies, Phoenix, Ariz., or SGE, Austin, Tex.

The capillary (3) can be jacketed to allow temperature control and removal of Joule heat produced during electrophoresis. Precise control of capillary temperature can also be achieved by introducing a heat exchange medium such as water, glycerol, etc. into the jacket. Also, to provide control or optimize electroosmotic flow, the inner wall of the capillary (3) can be chemically modified or passivated. For example, charges on the inner walls of the capillary can cause adsorption of the solutes to the inner wall, thereby interfering with the solute separation. By treating or chemically modifying the capillary with some substance, e.g., cetyltrimethylammonium bromide, hydroxyethylmethacrylate (HEMA), or trimethylchlorosilane, these effects can be minimized. Similarly, electroosmotic flow in capillary (3) can be controlled by applying an applied external electric field to the outside of the separation capillary wall. Various means can be used to apply the field. For example, the capillary (3) can be modified to contain an electrically conductive layer on the outside wall of the fused-silica capillary. Electrically conductive materials are typically gold, silver, platinum, aluminum, or graphite. The conductive layer is connected to a power supply. Typically, external fields ranging from −10000 V to +10000 V can be applied, altering the polarity and zeta potential on the inner wall of capillary (3). An alternative means of zeta potential control can be achieved by placing the capillary (3) inside a larger secondary tube (not shown), and introduce a buffer into the annular space between the outer wall of the capillary (3) and the inner wall of the tube. A power supply is connected by electrodes to the outside buffer layer. The polarity and zeta potential on the inner wall of the capillary (3) is then manipulated and varied by adjusting the external perpendicular field. Through control of the perpendicular field, the electroosmotic flow within the capillary (3) can be controlled and programmed to provide optimized analyte separation and recovery. Other modes of controlling electroosmosis include cooling the capillary, increasing the buffer molarity, or addition of a polymer to the running buffer to alter the viscosity of the electrolyte solution.

Capillary (3) is immersed in buffer reservoir (10), which contains separation buffer. Buffer composition should be optimized for the specific separation requirements, and may be the same or different from the sample diluent. A lower molarity of sample buffer of the same type as the separation buffer may also aid in sample stacking or narrowing the sample plug width. Generally, it is desirable to avoid siphoning within the capillary (3), caused by differential heights between the ends of the capillary. The siphoning can be minimized by maintaining the ends of capillary (3) at approximately the same height relative to each other.

After loading of the sample, the anode end of capillary (3) is returned to buffer reservoir (10), and an electric field is applied to capillary (3), causing the negatively charged bacteria to electrophorese or migrate toward the anode end of capillary (3). Voltage potentials may range from about 1 kV to 40 kV where a range of 10 kV to 30 kV is preferred. The terminating end of capillary tube (3) is also incorporated as part of the dispensing tip (8). The separation electrolyte contains cations, which when in contact with the inner wall of the fused-silica, moves the bulk flow of electrolyte toward the cathode end of capillary (3). As the bulk flow of the electrolyte moves toward the cathode end of (3), carrying with it the electrophoretically separated bacteria mixture, the separated zones are detected by detector (2) and the data is collected by the data collection means (1). Data collection means (1) can be a chart recorder or some type of data integrator with the ability to digitize signal for handshaking with computer (13).

The Data collection means (1) may be as simple as a strip chart recorder such as an ISCO model 615A which may be purchased from ISCO, Lincoln, Nebr.

Detection can be accomplished by means of a single or plurality of detectors (2). For example, detectors capable for use with capillary systems include visible and UV light absorbance, fluorescence, electrochemical, radioisotope and cell and particle counting detectors. Laser induced fluorescence and capillary coupled mass spectrometry systems, which afford newer modes of detection, provide means for ultra-sensitive detection. Another mode of detection, using laser-induced capillary vibration, a novel photothermal method, has been reported. Multi-wavelength detection, for continuous scanning, is also advantageous. Detectors can be clustered or separately located along the capillary. Thus, multiple parameters can be employed to characterize analyte populations, and the time dependence of the separation process can be detected. For the purposes of the present invention, UV detectors similar to Model V4 ultraviolet-visible absorbance detector (ISCO, Inc, Lincoln, Nebr.) are preferred.

Computer (13) can be any type, such as those personal computers maufactured by IBM or Apple, as long as it can "handshake" with robotics device (12) and together with software developed for computer (13) and robotics device (12), can perform the activities that are intended by the user, some of which are described below. Data collection systems suitable for use in the present invention are simliar to those provided by P/E Nelson, Cupertino, Calif.

As shown in FIG. 1 a high voltage power supply (6), is connected to electrodes (4) and (5). In a preferred embodiment, electrode (4) is the anode and electrode (5) is the cathode. However, it will be appreciated by one of skill in the art that if the applied field is reversed, the cathode becomes the anode. Power supplies suitable for use in the present invention are ones similar to Model LG80P1.5 power supply from Glassman High Voltage, (Whitehouse Station, N.J.). Generally, a power supply (6) is capable of delivering 0.1–60 kV. The electrodes (4), (5) are typically composed of an inert conductive material such as platinum, graphite or gold, where platinum is preferred. The anode electrode (4) is connected to and in contact with buffer reservoir (10) and the cathode electrode (5), is in contact with dispensing tip (8). Alternatively the cathode electrode (5), can also be in contact with dispensing tip reservoir (9) and in contact with a sample collection receptacle (11), via some x-y-z transport mechanism. Dispensing tip reservoir (9) is a receptacle for dispensing tip (8) and provides for sample collection and housing of dispensing tip(s) (8) while maintaining electrical continuity between capillary (3) and electrodes (4), (5).

Not shown in FIG. 1 is a protective enclosure with a protection barrier for the electrophoretic and analyte collection elements of the system. This enclosure protects and minimizes corona discharge due to ambient air currents and build-up of contaminating materials inside the chamber. Protection is especially important when the dispensing tip (8), which houses the terminating end of capillary (3), is transported between receptacles (9) and (11). It also provides a clean environment to minimize microbial contamination and dust particles. To insure against inadvertent personal contact with the high voltage electrical components, the enclosure comprises a safety interlocking mechanism that disables the power supply (6) when the protective enclosure is opened.

Robotic device (12) comprises sample collection receptacle (11), tip reservoir (9) and tip transport mechanism (24) and is in electrical communication with computer (13), and data collection device (1). Tip transport mechanism (24) provides a means of attaching and reversibly picking up and placing dispensing tip (8) in both sample collection receptacle (11) and tip reservoir (9). The timing and rate of movement of tip transport mechanism (24) and receptacle transport mechanism (25) are under computer control. Specifically, the tip transport mechanism (24) includes a tip clasp (7) for attachment to dispensing tip (8). By this means, dispensing tip (8) can be picked up and secured by the tip transport mechanism (24). In this way, dispensing tip (8) can be picked up and shuttled both within and between receptacles (9) and (11). The location, height and motion of tip (8) being variable and under precise time control by computer (13). In other words, robotic device (12) provides accurate means of X-Y-Z coordinate control over the dispensing tip location and movement.

Figure 2A:
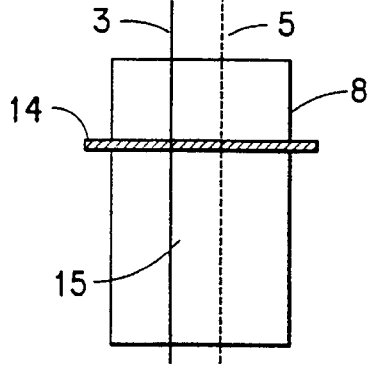
FIG. 2a is a cross-sectional view of a dispensing tip, which houses the cathodic end of a capillary and cathode electrode. On the dispensing tip is an attachment means, a device dispensing tip, a reservoir and a dispensing tip transport mechanism.

Dispensing tip (8) provides means of electroeluting and controlling collection of sample components. FIG. 2a is a cross-sectional view of dispensing tip (8), illustrating generic elements of the tip, including electrode (5), capillary (3), and dispensing tip docking fixture (14). Functionally, the dispensing tip provides means of proximally locating and electrically isolating electrode (5) and capillary (3) elements. Electrical isolation is important, both to avoid spontaneous discharge at high voltages and to avoid direct analyte transfer to the electrode, once electroeluted from the tip of capillary (3). The ends of electrode (5) and capillary (3) are further positioned to establish electrical continuity by contact of the tip with a conductive fluid.

In one embodiment the dispensing tip may be constructed by modification of Fiber-Tip pen such as those made by Hewlett Packard (#7746T). In modification, the interior components of the pen tip are removed and the pen center is then drilled out to permit insertion of a Teflon® sleeve drilled with two holes along the long axis for insertion of both the dispensing end (cathode end) of the capillary and the cathode electrode.

In an automated format, a plurality of dispensing tips could be simultaneously employed. In this mode, electrophoresis is started with dispensing tips located in a multi-position reservoir (9). As sample material is eluted from each capillary, the appropriate dispensing tip is shuttled to a predetermined location in sample collection receptacle (11) for the duration of analyte electroelution. The analyte could also be eluted using vacuum or pressure. The dispensing tip is then returned to (9). In this manner, multiple samples can be simultaneously processed.

Figure 2B:
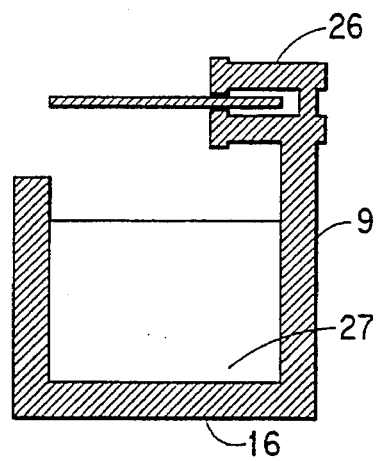
FIG. 2b is a cross-sectional view of a dispensing tip reservoir, illustrating a means of attachment to the dispensing tip. Also shown is a well containing fluid, which may serve as a collection receptacle or a dispensing tip positioner.
Figure 2C:
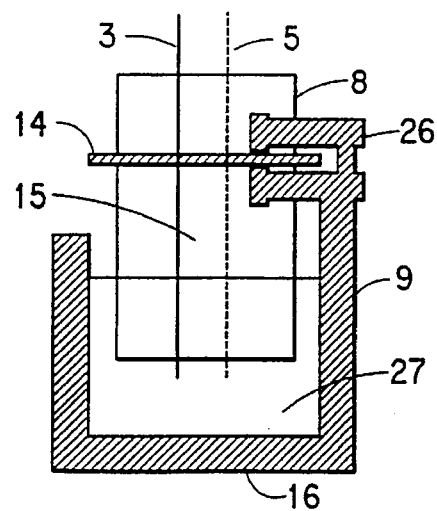
FIG. 2c illustrates the placement of a dispensing tip into a dispensing tip reservoir, showing attachment of a docking fixture to a docking fixture receptacle.

The dispensing tip reservoir (9) is illustrated in FIG. 2b and provides a means for containing the electrolyte fluid (27) and comprises a docking fixture receptacle (26) for receiving the docking fixture (14). Dispensing tip reservoir (9) can comprise a plurality of individual reservoirs in a circular or linear array. The array can be held or grouped in a holder. Optionally, the holder can be motorized and in communication with (13) to facilitate selective insertion and removal of dispensing tips. In this way, a plurality of different dispensing tips (8) can be in simultaneous use or single tip (8) can be moved sequentially between a plurality of reservoirs (9) wells, thus enabling collection of individual fractionation peaks.

In one embodiment the dispensing module was constructed by modifying various elements of a printer plotter such as those manufactured by Hewlett Packard (San Diego, Calif.). The cathode buffer reservoir and stationary dispensing tip holder may be constructed by modifying the revolving pen carousel of the printer plotter to both hold the dispensing tip describe above and provide means for an cathode buffer reservoir.

Contact of dispensing tip (8) with conducting fluids in dispensing tip reservoir (9) and collection receptacle (11) establishes electrical continuity. In this way, sample materials are electroeluted in collection fluid and not directly transferred to electrode (5). Appropriate positioning of (5) and (3) is achieved by interpositioning or surrounding the capillary with insulating materials, e.g., plastics, ceramics, Teflon® polymer or rubber. Docking fixture (14), facilitates attachment of the dispensing tip (8) to robotic device (12).

Figure 3:
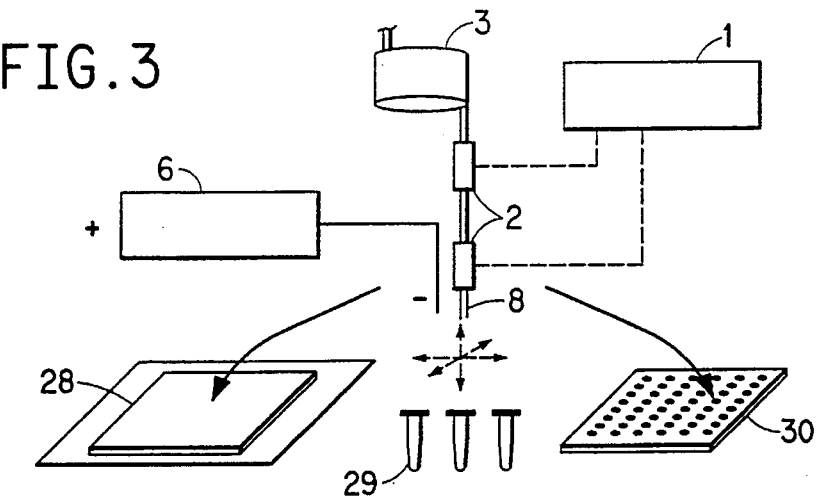
FIG. 3 is a diagrammatic representation of sample collection options, including cell collection onto nutrient agar gels, into tubes, or into multi-well plates.

Sample collection:

FIG. 3 illustrates several alternate methods of sample collection and in addition to diagramming the capillary (3), the data collection means (1), the detector (2), the power supply (6) and the dispensing tip (8), a sample collector receptacle support (28) along with sample tubes (29) and a multiwell plate (30) are shown. Sample collection receptacle (11) comprises a support (28), which further comprises an auxiliary support transport mechanism (25) in electrical communication with computer (13), capable of moving support (28) in concert with dispensing tip transport mechanism (24). Sample collection receptacle provides for receiving, distribution and compartmentalization of eluted sample materials. In some instances (11) can also facilitate analyte analysis by providing support suitable for cell propagation or analyte detection. In one embodiment sample components can be streaked onto a support (11) containing nutrient gels (28), collected in a support (11) containing tubes (29) or distributed in a support (11) containing an array of microwells (30). Optionally it is contemplated that support (11) may comprise a membrane.

Collection of analytes into tubes or wells could be for collecting fractions, where further processing would take place, e.g., the tubes could be temperature controlled and subsequent lysing of bacteria for DNA-RNA extractions, PCR and other amplification protocols, selective enrichment, biochemical testing for identification, or immunological assays can occur. Temperature controlled multiwell plates would increase sample throughput and increase the number of tests that could be performed. Another possibility would be to connect the dispensing tip to a commercial spiral plate streaker or some other type of cell counter, which would allow enumeration of bacterial colonies.

Generally, eluted sample materials can be transferred directly from capillary (3) to sample receptacle (11) by several mechanisms. Contact of dispensing tip (8) to a conductive fluid in the receptacle (11) establishes electrical continuity between capillary (3) and electrode (5). Eluting sample materials are then to be directly electroeluted into receptacle fluids. Alternatively, the receptacle support can be connected to electrode (5), receptacle (11) thus providing a functional ground. When tip (8) is brought in proximity with grounded receptacle (11), eluted samples are propelled by charge transfer to (11). In a further embodiment, tip (8) can be adapted with a piezoelectric oscillator mechanism which produces small droplets. As droplets are formed they are propelled in an atomizing spray onto the transfer support. In this way, sample materials can be transferred without direct contact. Piezoelectric oscillators suitable for this purpose are commercially available and simliar to those described in U.S. Pat. No. 5135852.

It is contemplated that in a specific embodiment data collection device (1) or detector (2) can be connected to computer (13). In this way, analytes that are detected could prompt computer (13) as to the mode and time of sample collection. For example, by analyzing the peak characteristics and retention time of the peak detected, a data collection device (1) and/or computer (13) could calculate the time of elution in/on a sample collection receptacle (11) and also how much of the sample will be dispensed per unit time. If multiple detectors are used, mixtures of analytes could be sorted by their individual characteristics, and routed to a specific sample collection receptacle (11) for further sample processing, depending on the process desired. Sorting could be accomplished by labeling individual analytes with a specific functional group or chromophore and detecting that specific wavelength. Detector (2) could be a photomultiplier tube and radiolabelled analytes could be sorted by different emission characteristics. Chemiluminescent labeled analytes could be sorted in the same manner and then-detected by a camera, film, thermoluminescent dosimeter, or any light capture mechanism. For example, chemiluminescent substrate concentrations could be varied on individual analytes, and variations of light emission could be used as an identifying marker of that analyte.

Cell identification and analysis:

Once the cells are transferred from the capillary onto a support, various identification strategies can be used to distinguish organisms. It is contemplated that in one embodiment cell identification takes the form of a biogram. In a preferred mode, the organisms are transferred directly onto a growth media. Alternatively, an array of zones, each containing a different growth media, might be employed. In this way, organisms requiring different growth conditions and nutrients can be detected.

Figure 4:
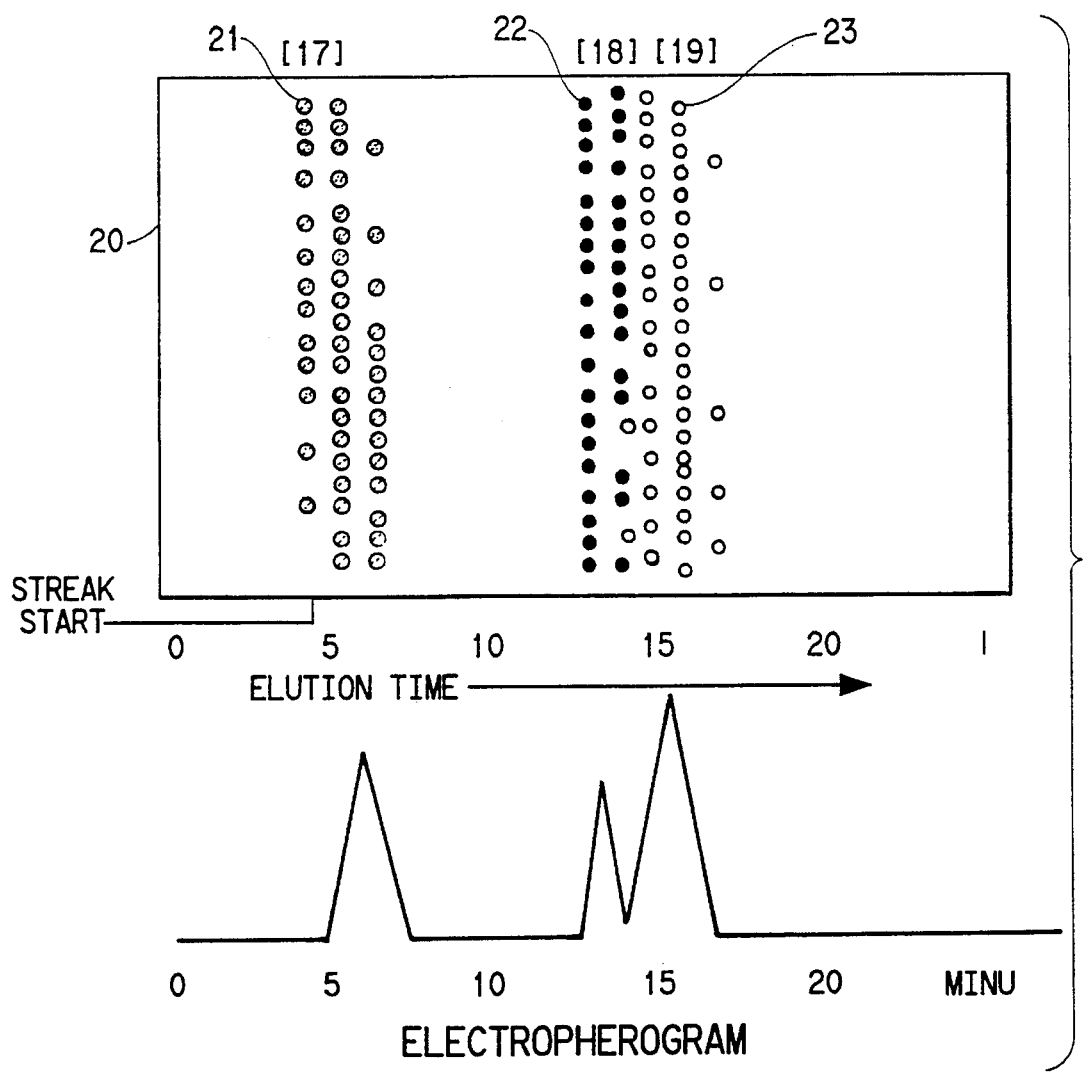
FIG. 4 is a schematic diagram of a "biogram", representing the deposition and growth of bacteria collected onto a nutrient agar gel plate.

FIG. 4 illustrates an actual biogram created for the identification and characterization of separated microorganisms. The "biogram" in FIG. 4 graphically depicts the separation of three bacterial strains, (21), (22), (23), dispensed onto nutrient agar support, and incubated to achieve bacterial growth. Bacterial strains (21), (22), and (23) correspond to the species *S. agalactiae, S. aureus*, and *R. capsulatis* respectively. Similarly, bacterial zones (17, 18, and 19) correspond to bacterial strains (21), (22), and (23), respectively. The shaded circles in FIG. 4 represent colonies arising for the growth of single cells collected during electrophoretic separation. It will be appreciated that the number of colonies and overlap of biogram cell populations (17), (18), (19) reflect both analytical resolution of the electrophoretic process and the viable cell density in each population. Analytically, cell collection tends to correlate directly with peak elution characteristics such as peak width and resolution. Cell densities reflect the integrated peak area. The array of cells in the biogram thus reflects the electrophoretic properties (e.g., elution time) of cells, detector and cell collection mode.

The biogram of FIG. 4 is created when a sample containing a mixture of living bacteria is electrophoretically separated and dispensed onto a support containing a nutrient agar media. Following incubation and cell growth, the resulting colonies form a "biogram" of the cell populations in the original sample. The profile of bacterial populations reflects the electrophoretic resolution, speed and streaking process.

In one embodiment nutrient gel plates may consist of agar media containing yeast extract and peptone layered on polyester plain paper such as that available from 3M Corp., St. Paul, Minn. The gel plates are further supported on a glass plate and centered under an aluminum frame.

In a preferred embodiment, collection of the bacteria onto the gel plate may be accomplished by programming the computer for streaking parameters before the run. The computer can be programmed to either detect a peak and calculate elution time automatically, or could be manually cued to start the collection when peaks are eluted as determined visually from the real time display. Streak parameters can be calculated based on the electroosmosis flow rate of the system and the expected elution time, and also by the width of peaks detected. After collection of the desired peaks, the dispensing tip was returned automatically to the cathode dispensing tip reservoir. The gel plate may be removed from the apparatus using sterile technique, and incubated for two days at 37° C. in a sterile container. Identification of the bacteria comprising the biogram is based on previous elutions with sample containing known species.

The "electrophoretic biogram" thus provides a unique and powerful method of analyzing the composition of mixed cell populations. Advantages of the method are that the relative abundance of different cell populations are conserved during the separation process. Recognition of the number of cells in each subpopulation and types of individual cells is aided by the combined information provided by detector(s) response during the separation process and cell growth characteristics (e.g. colony pigmentation and morphology). Once characterized, the density of subpopulations in the original sample tends to reflect the number of each species/strain and can be estimated by counting the number of colony types. The biogram thus provides an array of cells organized by their separation properties, detector response and mode of cell collection.

Alternatively cells can be collected on solid supports compatible with microscopic examination. In this mode of detection, collected organisms are detected directly without need for cell growth. Generally, prior to visualization cells undergo fixation treatment for the purpose of both immobilizing cells on the support and staining the cells to facilitates direct visualization. Many types of fixation process are widely practiced and depend on the method of visualization (e.g., light or electron microscopy) and are therefore well known to the routine user. Nevertheless, the known proximity of the cells enables a direct counting and correlation of cell morphology and electrophoretic properties of sample organisms. This process further permits immobilized cells to be reacted prior to or following electrophoretic collection with detection reagents such as tagged antibodies, nucleic acid probes, etc. These can be used to directly visualize cells by deposition of chromogenic, chemiluminescent, and fluorescent reporters.

In yet another embodiment, samples can be incubated with labeled materials suspected of being metabolized by the sample organism. Cells metabolize these radio-active, chromogenic or fluorogenic labeled materials, which can then be detected either during electrophoresis or following cell collection as a result of the accumulation these compounds or their products in or on the cells. In this manner organisms metabolizing a labeled compound could be detected by autoradiography, or image intensified luminescent and fluorescence image analyzers once deposited on the supports. An advantage of this method of identification is that cell populations containing unknown organisms can be screened for specific phenotypic markers or functional genes, and metabolic markers.

Different collection-strategies or modes of collection are useful in characterizing sample composition and for isolation of cells with specific phenotypic and genetic characteristics. Programmable computer control provides a versatile means of developing strategies for collecting and locating sample components following cell collection. While not intending to be restrictive, the following approaches illustrate generic strategies.

In one collection mode, eluted sample components can be deposited onto a sample collection support in a continuous streak pattern in which the end of the capillary is passed over the support at a programmed speed and streaking pattern, the speed and streaking pattern being programmable and under the control of the computer. In this mode, sample deposition simply reflects the organisms elution sequence. The position relative to the x,y coordinates on the support reflects the time and order of organism elution.

Alternatively, eluted materials can be deposited in discrete zones, the zones reflecting either detector response or elution profile. For example, detected sample components can be deposited or streaked in discrete zones according to the electrophoretic peaks and separation profile, each zone corresponding to a separate electrophoretic peak.

In a preferred embodiment, sample components can be sorted according to detector and/or electrophoretic response. In this mode, detected sample constituents are transported to specific locations in the sample collection support. For example, this is generally accomplished by a process in which an event is first detected. The predicted time of elution for the sample constituent is computed from the rate of analyte migration and distance of the detector from the exit tip of the capillary. Just before elution the capillary tip is moved via the capillary transport mechanism and sample constituent deposited in a specific location or tube. Following elution the capillary is then returned to its normal elution position. By these means individual cells or, population of like cells can be collected in discrete zones or locations. This mode of collection is useful in isolating cells or subpopulation of organisms possessing common phenotypic markers but possessing dissimilar electrophoretic properties.

It is anticipated those skilled in the art can utilize the versatility and capabilities of the applicants' invention to implement other sample collection strategies.

The following examples are meant to illustrate the invention but are not meant to be limiting in any way.

EXAMPLES

Bacteria strains and cell growth.

*Staphylococcus aureus* (ATCC 29213) was purchased from Difco Laboratories (Detroit, Mich.) as a MIC control kit. Streptococcal strains, *Enterococcus faecalis* (ATCC 29212), *Streptococcus pyogenes* (ATCC 19615), *Streptococcus agalactiae* (ATCC 13813), and *Streptococcus pneumonia* (ATCC 6303), were obtained from the American Type Culture Collection (Rockville, Md.). Organisms were aerobically cultured overnight at 37° C. in 3% Tryptic Soy Broth (TSB) or 3% Bacto Lactose Broth (LB), (Difco Labs, Detroit, Mich.). The starting cultures were then transferred to solid agar (2%) plates prepared with the above nutrient media. Cell cultures were 11 to 24 hours old when used unless otherwise indicated.

Sample Preparation.

Bacteria samples for electrophoresis were prepared using cells harvested from either a 1 mm dia. colony or 0.5 ml of the above culture broth. The harvested cells were transferred to 0.5 ml of the sterile Tris Borate buffer. The bacteria were pelleted for 3 min. using an Eppendorf (Model 5412) microfuge. The supernatant was removed and the cells resuspended in 250 μl of 0.05×buffer. (TBE) containing 4.45 mM Tris, 4.45 mM boric acid, 0.10 mM EDTA and adjusted to pH 9.5 with 10M KOH. The cell suspension was then recentrifuged. The wash procedure was repeated 2 times to remove culture media constituents. Bacteria were then resuspended in TBE buffer to form a sample containing approximately $10^9$ cells/ml. In this form, cell suspensions could be maintained at 4° C. for several days without appreciable change in electrophoretic response. Generally, $10^4$ to $10^6$ cells were injected for electrophoretic separation. For bacteria separations, prepared mixtures of bacteria that were separately cultured in nutrient media and then mixed were used for injection.

Strain Identification.

Bacteria recovered in electrophoretic fractions were identified by (a) metabolic fermentation using the BBL Minitek™ Identification System. (Becton Dickinson Microbiology Systems; Cockeysville, Md.); (b) serological identification of surface antigens with the Difco latex agglutination kit (Difco Labs, Detroit, Mich.); and by (c) cellular fatty acid composition. Fatty acid determinations on cells were performed by Microbial ID Inc., (Newark, Del.) using gas chromatographic analysis on cells harvested from 48 h slant cultures. Catalase activity (for *S. aureus*) was determined by immersing colonies in a 3% aqueous solution of hydrogen peroxide. Immediate evolution of bubbles indicated a catalase-positive test.

Microscopy.

The degree of cell assemblage of bacteria collected from electrophoretic fractions was determined using a Nikon Diaphot-TMd. inverted microscope equipped with 100×1.25 N.A. phase contrast objective, ELWD 0.3 condenser, and a Dage 81 video camera. Video-micrographs of bacteria were obtained using a Sony Mavigraph Video Printer. Cell numbers were determined in a Petroff Hauser counting chamber using a light microscope. In some cases, cells were counted automatically using an Olympus Q2 image analyzer equipped with a Compaq 386/25 computer.

EXAMPLE 1

Electrophoretic Apparatus and Separation Conditions

FIG. 5a illustrates one implementation of the instrumentation portion of the experimental setup used to achieve bacterial separations in capillary zone electrophoresis. Separations were performed in a separation zone formed by a 250 cm length of 100 μm id. polyimide-clad fused silica capillary (Polymicro Technologies, Phoenix, Ariz.) which was filled with a dilute solution of TBE buffer. The detector was positioned 225 cm from the anode (injection) end of the capillary. TBE is a standard biological buffer and 1× TBE consists of 90 mM tris-hydroxymethylaminomethane, 90 mM boric acid, and 2 mM ethylenediaminetetraacetic acid, disodium salt. For typical bacterial separations, 0.05×TBE was used, though other concentrations could be utilized as well. The ends of the separation capillary were immersed in reservoir vials containing 25 ml of 0.05×TBE buffer. Also immersed in the reservoirs of the buffer were two platinum electrodes (20 gauge platinum wire, 5 cm lengths), which were in turn connected to the output terminals of a high voltage power supply (HV). A Model LG80P1.5 power supply from Glassman High Voltage, (Whitehouse Station, N.J.) was used. Approximately 15 cm from the cathode (or grounded) end of the capillary, a detection window was formed on the capillary by burning the protective polyimide coating from the exterior of the capillary with a propane flame.

This detection window was positioned in the optical path of a modified Model V4 ultraviolet-visible absorbance detector (ISCO, Inc, Lincoln, Nebr.). The conventional flow cell of the UV-vis detector was replaced with an adjustable pinhole mount attached to a precision translation stage (Oriel Corporation, Stratford, Conn.), which facilitated alignment of the pinhole with the capillary and allowed the pinhole/capillary assembly to be reproducibly positioned at the focal point of the optical beam in the detector. Detection was accomplished at 190–200 nm through the unclad section of the capillary used as an absorbance cell (observation volume of ~120 picoliters). The signal from the detector was fed to a strip chart recorder and simultaneously digitized and stored on a computer-based data collection system (P/E Nelson, Cupertino, Calif.).

Injections of bacterial samples were by timed hydrostatic injection (ca. 20–30 s at 25 cm head pressure) at the anode. After injection, the anode end of the capillary was returned to the anode buffer reservoir and the high voltage was gradually applied across the capillary in a 5 minute linear ramp from 2 to 30 kV, where it was held for the duration of the run; current through the capillary was typically 4–5 μA. The developing separation took place down the length of the capillary and was recorded at the previously-described detector window by a combination of UV absorbance and light-scattering. Before separation, the capillary was first cleaned and sterilized by successively drawing through the capillary 1N KOH, water, ethanol, sterile deionized water and sterile 0.05×TBE electrophoresis buffer.

EXAMPLE 2

Electrophoretic separation of *S. agalactiae* and *S. pneumoniae*

This example demonstrates that two species of the genus of Streptococcus bacteria may be completely separated by the electrophoretic apparatus and method described in Example 1.

Figure 6:
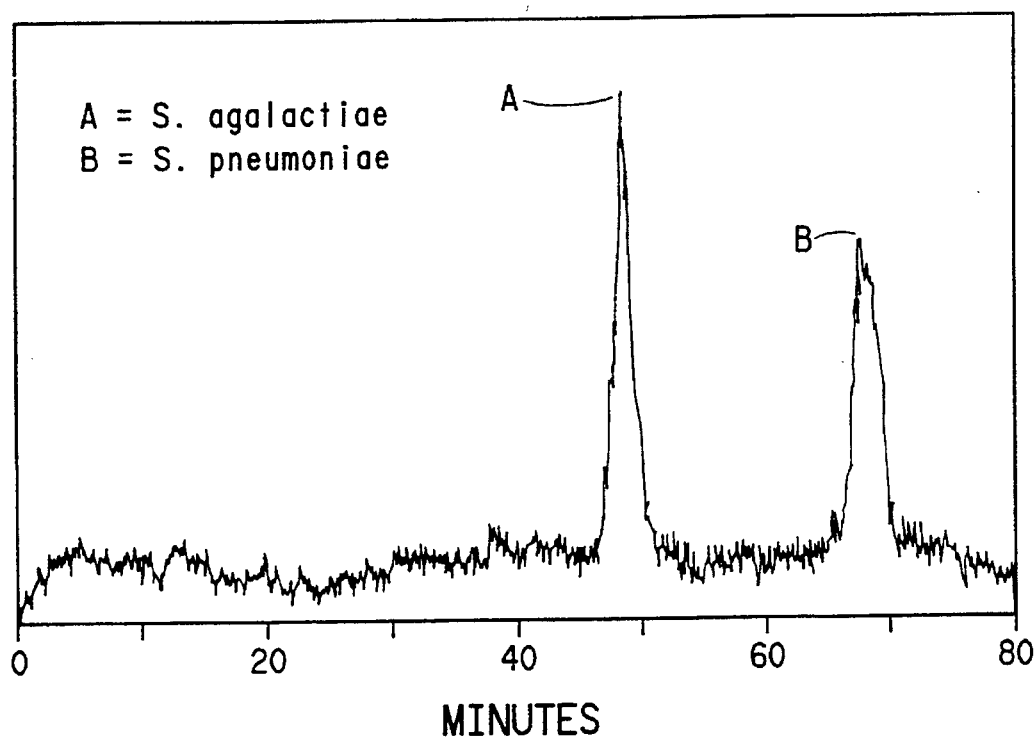
FIG. 6 is a strip chart recording of the electrophoretic separation of S. agalactiae and S. pneumoniae.

A sample of a mixture of *S. agalactiae* and *S. pneumoniae* was injected into the separation capillary as described in Example 1 and eluted under conditions described above. Prior to the electrophoresis of the bacterial cell mixture, each species was electrophoresed individually to determine the electrophoretic migration time. FIG. 6 is the output of a strip chart recording of the separation run. As can be seen in FIG. 6, there is a clear separation of the two bacterial strains where the migration time as noted on the abscissa of the trace is characteristic of the species of bacteria, and the magnitude of the peak (peak height above baseline and/or peak area) is indicative of the quantity of bacteria contained within the band. Under the specific set of conditions utilized for this separation, a migration time of 48 minutes is characteristic of S. agalactiae and a migration time of 66–68 minutes is characteristic of S. pneumoniae.

EXAMPLE 3

Electrophoretic separation of S. pyogenes and S. pneumontae

This example demonstrates that two species of the genus of Streptococcus bacteria may be completely separated by the electrophoretic apparatus and method described in Example 1.

Figure 7:
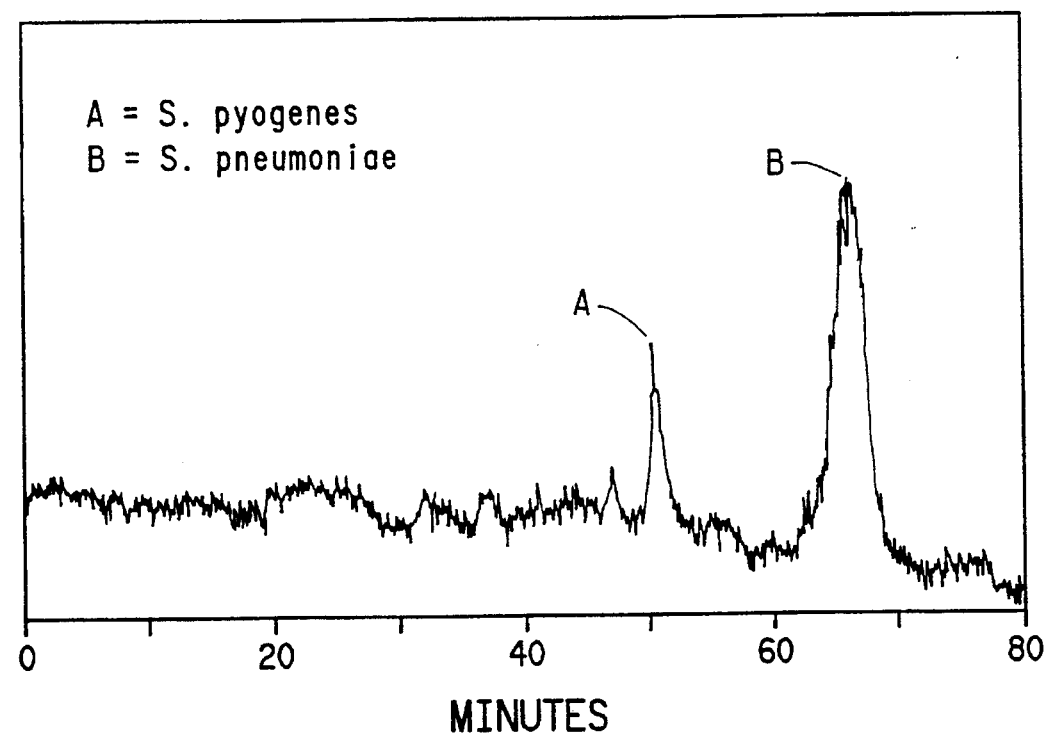
FIG. 7 is a strip chart recording of the electrophoretic separation of S. pyogenes and S. pneumoniae.

A sample of a mixture of S. pyogenes and S. pneumoniae was injected into the separation capillary as described in Example 1 and eluted under conditions described above. Prior to the electrophoresis of the bacterial cell mixture, each species was electrophoresed individually to determine the electrophoretic migration time. FIG. 7 is the output of a strip chart recording of the separation run. As can be seen in FIG. 7, there is a clear separation of the two bacterial strains where the migrations time as noted on the abscissa of the trace is characteristic of the species of bacteria, and the magnitude of the peak (peak height above baseline and/or peak area) is indicative of the quantity of bacteria contained within the band. As in Example 2, a migration time of 66–68 minutes is characteristic of S. pneumoniae, whereas a migration time of 50 minutes is indicative of S. pyogenes.

EXAMPLE 4

Electrophoretic separation of a complex mixture of S. agalactiae, E. faecalis and S. pneumoniae This example demonstrates that a variety of species and morphologies of the genus of bacteria Streptococcus and ehterococcus may be completely separated by the electrophoretic apparatus and method described in Example 1.

Figure 8:
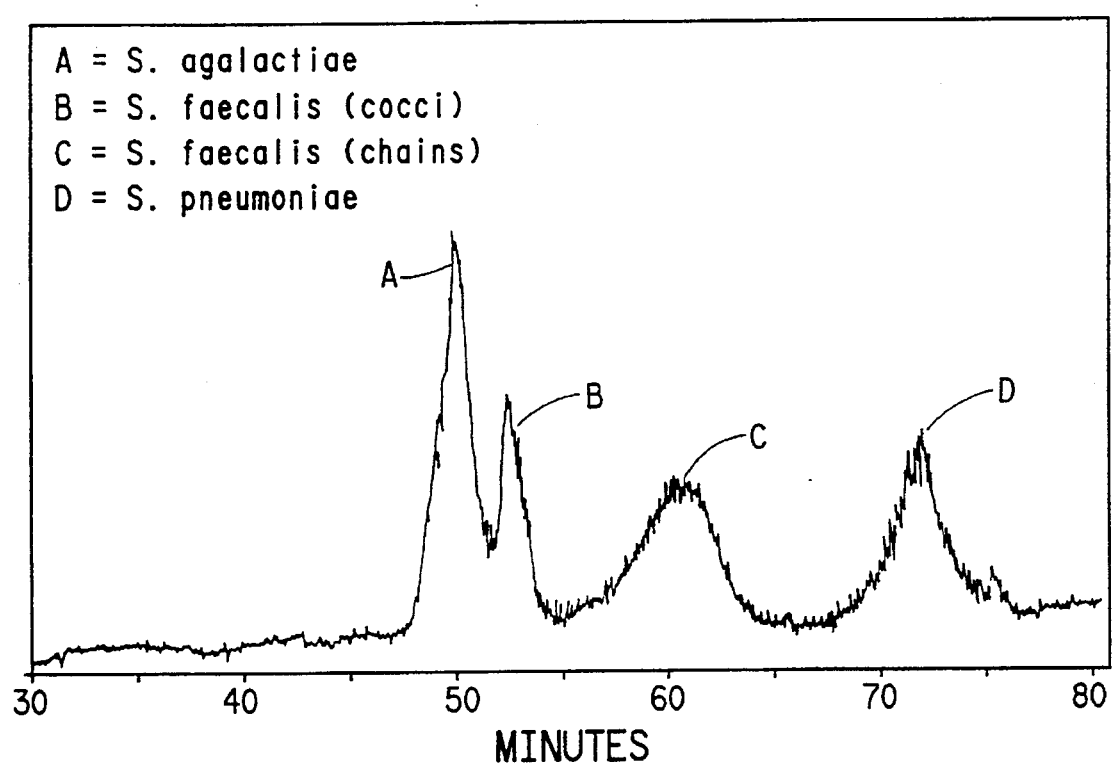
FIG. 8 is a strip chart recording of the electrophoretic separation of S. agalactiae, S. faecalis and S. pneumoniae.

A sample of a mixture of S. agalactiae, E. faecalis, and S. pneumoniae, where E. faecalis existed in both chain and cocci morphology, was injected into the separation capillary as described in Example 1 and eluted under conditions described above. Prior to the electrophoresis of the bacterial cell mixture, each species and morphology was electrophoresed individually to determine the electrophoretic migration time. FIG. 8 is the output of a strip chart recording of the separation run. As can be seen in FIG. 8, there is a clear separation of the three bacterial species where the migration time as noted on the abscissa of the trace is characteristic of the species of bacteria, and the magnitude of the peak (peak height above baseline and/or peak area) is indicative of the quantity of bacteria within the band. The figure shows two distinct peaks that can be identified as two separate entities in the E. faecalis sample. These two peaks in the E. faecalis sample were identified as morphologically different E. faecalis bacterial assemblages, with the sharp, early eluting peak containing monomeric and dimeric assemblages whereas the broader, slower-migration peak was composed of larger chain assemblages of the E. faecalis bacteria.

EXAMPLE 5

Electrophoretic separation of Staphylococcus aureus and D. desulfuricans

This example demonstrates that different bacterial genera may be completely separated by the electrophoretic apparatus and method described in Example 1.

Figure 9:
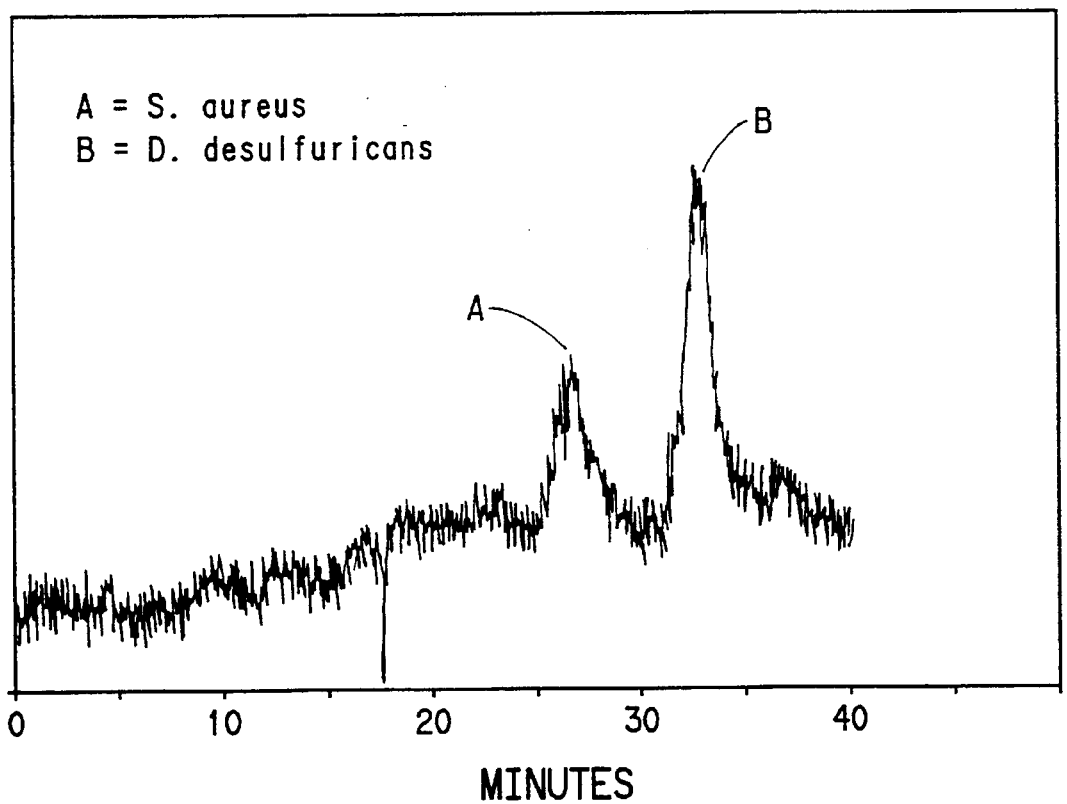
FIG. 9 is a strip chart recording of the electrophoretic separation of S. aureus and D. desulfuricans.

A sample of a mixture of Staphylococcus aureus and D. desulfuricans were injected into the separation capillary as described in Example 1 and eluted under conditions described above. Prior to the electrophoresis of the bacterial cell mixture, each species was electrophoresed individually to determine the electrophoretic migration time. FIG. 9 is the output of a strip chart recording of the separation run. As can be seen in FIG. 9 there is a clear separation of the two bacterial species where the migration time as noted on the abscissa of the trace is characteristic of the species of bacteria, and the magnitude of the peak (peak height above baseline and/or peak area) is indicative of the quantity of bacteria contained within the band.

EXAMPLE 6

Electrophoretic separation of Staphylococcus aureus and Streptococcus pneumoniae This example demonstrates that different bacterial genera may be completely separated by the electrophoretic apparatus and method described in Example 1. Additionally example 6 demonstrates that fractions of separated bacteria may approach 100% purity.

A sample of a mixture of Staphylococcus aureus and Streptococcus pneumoniae was injected into the separation capillary as described in Example 1 and eluted under conditions described below. Prior to the electrophoresis of the bacterial cell mixture, each bacteria was electrophoresed individually to determine the electrophoretic migration time. The electrophoretic separation indicated a clear separation of the two bacteria.

Fractions from the electrophoresis run were collected and analyzed for bacterial purity. The collection process consisted of calculating the time to peak elution ($t_e$) for each peak using the proportionality between the time to detection ($t_d$) for the specific peak, the total length of the capillary ($l_t$), and the distance from the injection end to the detector ($l_d$):

$$t_e = t_d (l_t)/(l_d) \tag{1}$$

Figure 10:
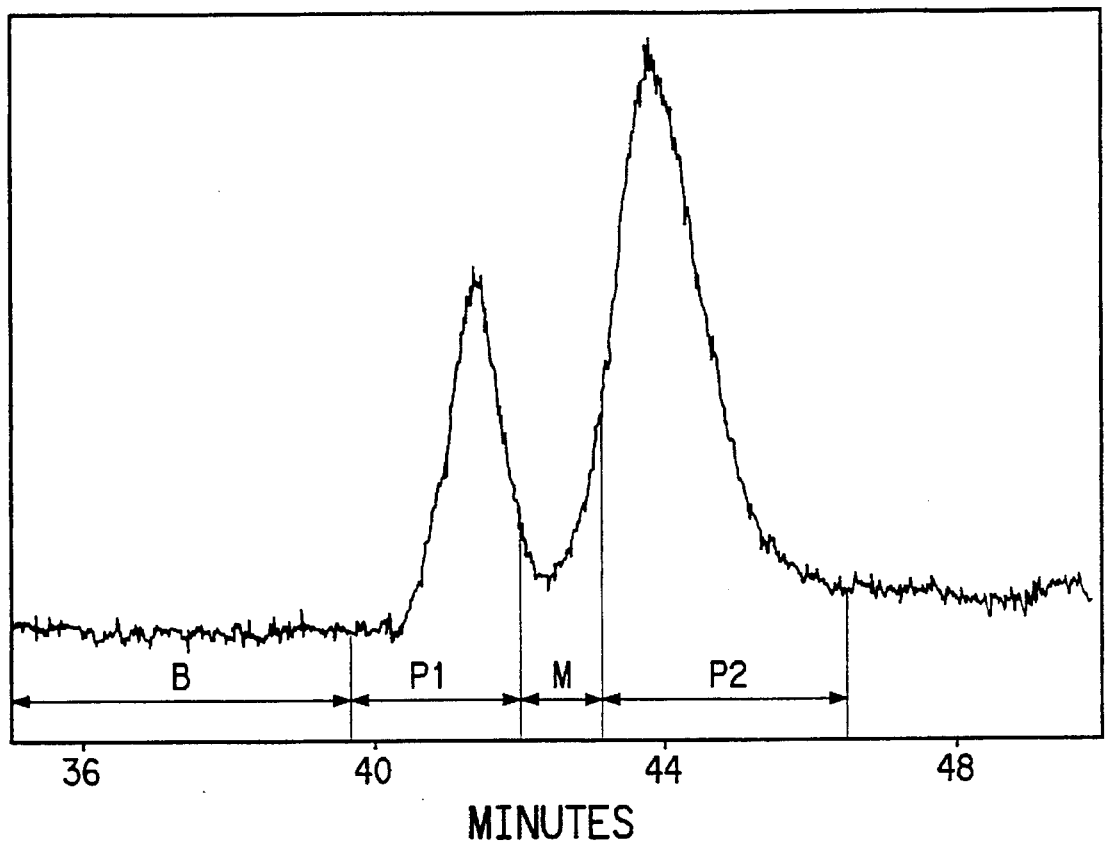
FIG. 10 is a strip chart recording of the electrophoretic separation of S. aureus and S. agalactiae illustrating the location of fractions taken for purity analysis.

At time $t_e$, the cathode end of the capillary was removed from the cathode buffer reservoir, placed in a collection tube containing a Pt wire immersed in 10 μl of 0.05×TBE buffer and connected to the cathode. After collection of the desired peak, the capillary was reinserted into the 25 ml cathode buffer reservoir. At precalculated times during the course of the separation in FIG. 10, application of the high voltage to the anode end of the capillary was momentarily interrupted and the cathode end of the capillary was removed from the electrolyte reservoir and placed in a microcollection tube. The high voltage was reinstated across the length of the capillary and a fraction of the effluent from the separation capillary containing a portion of the separated bacteria was collected into the microcollection tube for a precalculated duration of time. The microcollection tubes Were fabricated from Eppendorf Gel-Loader pipette tips, (Brinkmann Instruments, Westbury, N.Y.) which were flame sealed at the normal dispensing end of the tip forming a microtube, and fitted with a 36-gauge platinum wire, 5 cm long, and at the time of collection, was connected to the cathode electrode to form the cathode buffer reservoir. The assembled microcollection tubes were sterilized by autoclaving and maintained under aseptic conditions prior to use. At the end of the predetermined collection time, the cathode end of the capillary was briefly swabbed with aqueous ethanol to sterilize the exterior of the capillary which might have been contaminated with bacteria. The capillary was then reinserted into another microcollection tube and the next fraction of the separation collected. This process was repeated numerous times, thereby obtaining predetermined fractions of the separated bacteria. The various collected fractions from the separation as well as appropriate control and blanks samples of bacteria were then exponentially diluted and cultured on TSB agar plates. The plates were counted and quantitated on an automatic plate counting instrument (Artek Model 880 Counter, Dynatech Lab, Chantlily, Va.), Quantitative analyses of the fractions collected from the *S. aureus/S. pneumoniae* separation are shown in Table I below.

strains, each strain being readily distinguished by either colony morphology or simple chemical test, e.g., catalase activity. The mixtures were prepared by harvesting and transferring roughly equivalent cell masses from 11 h solid cultures of the organisms to 0.5 ml of TBE buffer. The mixtures were electrophoretically separated using the above conditions and recorded via a chart recorder as show in FIG. 10. As shown in FIG. 10 the two bacterial peaks (P1 and P2) were collected along with fractions corresponding to the regions before (B) and mid-way (M) between the elution of bacterial peaks. Control samples of the original mixtures (C) and the buffers in the anode reservoirs (R) were also examined for bacteria type and number.

During separation, electrophoretic fractions representing the bacteria peaks and regions before, between, and after the peaks were collected. Following separation, cell fractions were quantitatively transferred under aseptic conditions into 0.5 ml of 0.05×TBE buffer. The fractions were then serially diluted with the TBE buffer and portions (0.2 ml) of each dilution were uniformly spread on Tryptic Soy agar plates. After overnight incubation at 37° C. the number of colonies

TABLE I

| Electrophoretic Fraction | Cells Collected | S. aureus Cells | Fraction Purity | S. pneumoniae Cells | Fraction |
| --- | --- | --- | --- | --- | --- |
| Before Peak (B) | 0 | 0 | | | |
| Peak 1 (P1) | 140,750 | 140,750 | 100% | 0 | 0.0% |
| Mid. Peak (M) | 64,260 | 12,250 | 19.1% | 52,010 | 80.9% |
| Peak 2 (P2) | 10,262 | 150 | 1.5% | 10,112 | 98.5% |
| Control (C) | 217,500 | 155,000 | 71.3% | 62,500 | 28.7% |

The data indicate that the fraction corresponding to peak 1 (P1) is 100% pure *S. aureus*, with no contaminating *S. pneumoniae* present in the collected fraction. The mid-fraction (M), corresponding to the material in the valley between the two peaks, is impure as would be expected, containing both the *S. aureus* and *S. pneumonia* bacteria. The fraction corresponding to P2 is also essentially pure, of each strain on the plates were identified by colony morphology and counted using an Artek Model 880 counter (Dynatech Labs, Chantilly, Va.). The efficiency of separation was then determined from the percentage of each organism in the peaks as shown in Table II below.

TABLE II

| Electrophoretic Fraction | Cells Collected | S. aureus Cells | Fraction Purity | S. agalactiae Cells | Fraction Fraction |
| --- | --- | --- | --- | --- | --- |
| Before Peak (B) | 0 | 0 | | 0 | |
| Peak 1 (P1) | 12,012 | 19 | 0.2% | 11,993 | 99.8% |
| Mid. Peak (M) | 24,924 | 4,162 | 16.7% | 20,762 | 83.3% |
| Peak 2 (P2) | 8,666 | 8,566 | 98.9% | 100 | 1.1% |
| Control (C) | 50,755 | 20,043 | 39.5% | 30,712 | 60.5% | containing 98.5% *S. pneumoniae* and only 1.5% *S. aureus*. This purity represents a substantial purification of the *S. pneumoniae*, since it was the minor component in the original bacterial mixture, present initially at a concentration of 28.7%.

EXAMPLE 7

Cell Separation Efficiency

The strain contamination between electrophoretic peaks was further investigated by separating mixtures of bacteria exhibiting overlapping electrophoretic peaks (*S. agalactiae—S. aureus*) as shown in FIG. 10. Each mixture contained roughly equal proportions of two different bacterial It is clear from the data in Table II that the (B) fraction is free of bacteria. This demonstrates that capillary sterilization, fraction collection procedures and assay protocols were aseptic and effective in preventing bacterial contamination. In addition, the leading peak (P1) was homogeneous containing only one type of bacteria. As expected the mid-fraction (M) contains mixtures of bacteria present in P1 and P2.

EXAMPLE 8

Determination of Bacteria Survival and Recovery

Cells harvested from 11 h cultures of *S. aureus, E. faecalis, S. agalactiae*, and *S. pneumoniae* were separately electrophoresed in triplicate experiments. During electrophoresis, the effluent from the capillary column was collected in 3 fractions comprising the cell peak and effluents preceding and following the bacteria peak. Using identical conditions, cell samples were also introduced into the capillary and then backflushed into a known volume of 0.05× TBE buffer to serve as total cell control samples. The recovered cell fractions and controls were quantitatively transferred under aseptic conditions into 0.5 ml of 0.05× TBE buffer. The fractions were then serially diluted with 0.05×TBE buffer and portions (0.2 ml) of each dilution spread uniformly on Tryptic Soy agar plates. After overnight incubation at 37° C., colonies were counted on an Artek Model 880 counter (Dynatech Labs, Chantilly, Va.). The number of viable cells in the samples and the percentage of cells recovered in each fraction are. illustrated in Table III below.

TABLE III

| Bacteria | Electrophoretic peak (Avg. % Recovery) | Anode Reservoir (Avg. % Recovery) | Total (Avg. % Recovery) |
| --- | --- | --- | --- |
| E. faecalis | 80 | 35 | 115 |
| S. pneumoniae | 84 | 12 | 96 |
| S. agalactiae | 63 | 58 | 121 |

Total % recover was a function of the number of bacteria eluted in the electrophoretic peak minus the number still left in the anodic reservoir. As can be seen by the data in Table III there is high recovery of all bacterial species by this method.

EXAMPLE 9

Robotics Cell Collection System

For sake of illustrating the cell separation and collection principle, a robotics cell sorting and collection apparatus was assembled using three apparatus modules. The elements of the electrophoretic separation module consisted of a Glassman LG-80D high voltage power supply (Whitehouse Station, N.J.), connected to platinum wire electrodes (30 gauge). Detection was accomplished using a modified ISCO V4 UV capillary absorbence detector (Lincoln, Nebr.). Output for the detector, measured at 200 nm, was recorded on an ISCO Model 615A chart recorder. The separation capillary consisted of a Polymicro Technologies (Phoenix, Ariz.) polyimide coated fused-silica capillary (350 μm O.D., 75 μm I.D.) 180 cm in length, 90 cm to the detector. A flow cell was formed by removing a portion of the polyimide coating to create a 0.5 cm transparent detection window. The capillary window was then mounted in the detector and the anode end of the capillary connected to the anode buffer reservoir. The other end of the capillary was attached to a dispensing tip constructed by modification of a Fiber-Tip pen (Hewlett Packard #17746T). In modification, the interior components of the pen tip were first removed. The pen center was then drilled out to permit insertion of a Teflon® polymer sleeve drilled with two holes along the long axis for insertion of both the dispensing end (cathode end) of the capillary and the cathode electrode. The tip end of the Teflon® sleeve was machined larger than the centering hole in the pen tip and with a curved end. Hole sizes were machined to provide pressure fits between Teflon® sleeve and the pen tip and between the Teflon® sleeve and the electrode and the capillary, the capillary and electrodes holes being separated to provide for electrical isolation. Assembly of the dispensing tip was then accomplished by first feeding the ends of the capillary and electrode through the modified pen tip. The ends of the capillary and electrode were then carefully inserted through the Teflon® sleeve so that the ends extended ca. 0.01" beyond the sleeve. The Teflon® sleeve was then inserted into the modified pen tip to complete the assembly of the dispensing tip. In designing the Teflon® sleeve, the distance from the dispensing tip holder to the end of the tip was adjusted so that when in contact with surface of the collection gel, the dispensing tip remained essentially perpendicular to the surface of the collection gel. In this way, uniform cell dispensing was achieved regardless of the direction and speed of tip movement.

The robotics cell sorting and dispensing module was constructed by modifying a printer plotter (Hewlett Packard 7475A plotter, San Diego, Calif.). The cathode buffer reservoir and stationary dispensing tip holder was constructed by modifying the revolving pen carousel of the 7475A plotter to both hold the dispensing tip described above and provide means for a cathode buffer reservoir. This was accomplished by enlarging the rubber pen boot (HP #07475-60038)to enable facile insertion and removal of the dispensing tip. Electrode buffer (ca. 50 μl) was then added to each boot provide means of electrical continuity between the cathode and the end of the capillary. The electrode dispensing tip was then place in the revolving carousel pen holder mechanism. Spring tension in the dispensing tip holder was adjusted to prevent the dispensing tip from gouging the nutrient agar gel during movement across the plate. To prevent buffer siphoning effects, the cathode end of the capillary was maintained level with the height of the buffer fluid in the anode buffer reservoir. The integrated cell collection and electrophoretic modules were enclosed in a Lucite™ enclosure fitted with a magnetic shut off switch to prevent inadvertent contact or electrical discharge.

Bacteria strains and cell growth

*Staphylococcus aureus* (ATCC 29213) was purchased from Difco Laboratories (Detroit, Mich.) as a MIC control kit. *Streptococcus agalactiae* (ATCC 13813) was obtained from the American Type Culture Collection (Rockville, Md.). Photosynthetic bacterium *Rhodobacter capsulatis* strain #551003 was obtained in-house. Organisms were aerobically cultured-overnight at 37° C. in 3% Tryptic Soy Broth (TSB) or 3% Bacto Lactose Broth (LB), (Difco Labs., Detroit, Mich.), except for the Rhodobacter, which was grown in minimal media (0.3% yeast extract, 0.3% peptone, and 1.5% agar) at 35° C. for two days. Frozen suspensions of *Staphylococcus aureus* and *Streptococcus agalactiae* were transferred to solid minimal media YE plates (1.5% agar). Cell cultures were 11 to 24 h old when used unless otherwise indicated.

Sample Preparation

Bacterial samples for electrophoresis were prepared using cells harvested from YE plates. Colonies from each plate were resuspended in 500 μl of 0.05×TBE (pH 9.5). Each tube contained about $10^{12}$ bacteria/ml. Ratios for each organism were determined empirically by performing two separations before collection onto agar. Aliquots of 15 μl *S. agalactiae*, 5 μl *S. aureus* and 15 μl *R. capsulatis* were combined to make up the sample for electrophoresis and collection onto the nutrient agar gel plate.

Nutrient Agar Gel Plates

Nutrient gel plates were prepared by pouring melted sterile solution (ca. 150 ml) containing 0.3% yeast extract, 0.3% peptone and 1.5% agar onto 8.5"×11" polyester plain paper 688 copier film (3M Corp., St. Paul, Minn.) supported on a 13"×11" glass plate and centered under a 1/16" thick aluminum frame constructed with interior cut out opening of 7⅝"×10". The aluminum frame center over the film provide a ca. ½" perimeter margin around the film support which is not coated with agar. Once the agar is cast onto the film, a second glass plate is used to cover the agar during hardening and storage.

Electrophoretic Separation and Collection

Separation of the 3 bacteria mixture and subsequent collection onto nutrient YE gel plate was performed on the previously described robotic cell collection module. Injection of the sample was at the anode end of the capillary by siphoning for 15 seconds at 25 cm head pressure. After loading the sample, the anodic end of the capillary was placed back into the 25 ml buffer reservoir containing 0.05×TBE buffer (pH 9.5). The dispensing tip assembly containing the cathode electrode and capillary was placed in the modified rubber boot, containing 50 μl of 0.05×TBE buffer. A voltage of 30 kV was applied across the capillary and held constant for the duration of the run; current through the capillary was typically 1 μ. Before separation, the capillary was rinsed with 0.1M NaOH for 5 minutes, distilled, deionized H$_2$O for 5 minutes, and 0.05×TBE buffer for 5 minutes.

Automated Cell Collection

For collection of the bacteria onto the gel platel, the computer was programmed for streaking parameters before the run. This consisted of setting the streak length (20 cm), speed of the dispensing tip (1 cm/second), and distance between each streak line (8 mm). The computer can be programmed to either detect a peak and calculate elution time automatically, or could be manually cued to start the streaks when peaks are eluted as determined visually from the real time display. Streak parameters can be calculated based on the electroosmosis flow rate of the system and the expected elution time, and also by the width of peaks detected. After collection of the desired peaks, the dispensing tip was returned automatically to the cathode dispensing tip reservoir. The gel plate was removed from the apparatus using sterile technique, and incubated for two days at 37° C. in a sterile container.

Analysis of the Gel Plate

Three distinct zones of bacteria were observed. The first zone consisted of white colonies in which growth started at the approximate elution time expected. There was some overlapping of the first zone and the second zone, which is expected, due to the closeness of the first two peaks. The second zone which corresponded in time to the peak width on the real time display, consisted of white-yellowish colonies. The third zone consisted of red colonies, again with some overlapping due to the closeness of peak two and peak three. The elution order, which was determined previously by the migration times of each bacteria run alone, was *S. agalactiae*, *S. aureus*, and *R. capsulatis*. The gel plate showing these zones is schematically represented in FIG. 4.

We claim:

1. A method of sorting and detecting viable microorganisms and cell populations, while maintaining viability of said microorganisms and cell populations, comprising:
    (a) introducing a mixture of viable microorganisms or cell populations or microorganisms and cell populations into one end of a cell separator being comprised of:
        (i) a small capillary separation tube having a chargeable inner surface which will develop and hold a net negative or positive charge under the influence of an electric field;
        (ii) an anodic electrode positioned at a first end of said tube;
        (iii) a cathodic electrode positioned at a second end of said tube;
        (iv) an electrolyte solution filling said tube and contacting both said anodic and said cathodic electrodes wherein said electrodes are maintained in electrical communication with each other and said tube;
    (b) applying an electrical potential of between about 1 and 40 Kv across said electrodes whereby both an electrophoretic force and an electroosmotic force is produced within said electrolyte solution;
    (c) allowing migration of the viable microorganisms or cell populations to occur wherein the microorganisms or cell populations are sorted; and
    (d) detecting said migrated viable microorganisms or cell populations.

2. A method according to claim 1 wherein said chargeable inner surface is silica.

3. A method according to claim 1 wherein said viable cell populations are bacteria.

4. A method according to claim 1 wherein the charge of said chargeable inner surface is maintained independently of the charge of said electrolyte solution.

5. A method according to claim 4 wherein the charge of said chargeable inner surface is maintained independently by applying a second electric field to an outside wall of the capilary.

6. A method according to claim 1 wherein said capillary has a length from about 0.1 to 5 meters and an internal diameter from about 5 to 200 microns.

7. A method according to claim 6 wherein said electroosmotic force may be varied in a controlled fashion.

8. A method according to claim 1 wherein said capillary has a length from about 10 cm to 250 cm and an internal diameter of about 25 to 150 microns.

9. A method of sorting viable microorganisms and cell populations comprising the steps of:
    (i) providing a microorganism or cell population collecting system further comprising:
        (a) a movable fraction dispensing device capable of dispensing small volume fractions;
        (b) a detector means operably connected to said dispensing device and capable of detecting the presence of viable microorganisms or cell populations in said dispensing device;
        (c) a computer for the coordination of said detector and said dispensing device; and
        (d) a solid growth medium capable,of supporting the growth of microorganisms or cell populations;
    (ii) moving said dispensing device in a specific pattern above said growth medium in response to the detection of viable microorganisms or cell populations in said device;
    (iii) collecting said fractions containing said viable microorganisms or cell populations on said solid growth medium;

(iv) incubating said growth medium for a time sufficient to produce individual colonies of viable microorganisms or cell populations;

(v) analyzing said colonies for the presence of specific microorganisms or cell populations.

10. The method of claim 9 wherein the solid growth medium is in a form selected from the group consisting of a tube, a micro-well and a membrane.

* * * * *